(12) United States Patent
Matsuyama et al.

(10) Patent No.: US 7,829,306 B2
(45) Date of Patent: *Nov. 9, 2010

(54) PROTEIN HIGHLY PRODUCING RECOMBINANT ANIMAL CELL, METHOD FOR PREPARING THE SAME, AND METHOD FOR MASS-PRODUCING PROTEIN USING THE SAME

(75) Inventors: Reiko Matsuyama, Kikuchi (JP); Hiroaki Maeda, Kikuchi (JP); Hitomi Shirahama, Kikuchi (JP); Takayuki Imamura, Kikuchi (JP); Yasuharu Kamachi, Kikuchi (JP)

(73) Assignee: Juridical Foundation the Chemo-Sero-Therapeutic Research Institute, Kumamoto (JP)

( * ) Notice: Subject to any disclaimer, the term of this patent is extended or adjusted under 35 U.S.C. 154(b) by 365 days.

This patent is subject to a terminal disclaimer.

(21) Appl. No.: 10/576,978

(22) PCT Filed: Oct. 21, 2004

(86) PCT No.: PCT/JP2004/015594

§ 371 (c)(1),
(2), (4) Date: Nov. 12, 2008

(87) PCT Pub. No.: WO2005/040364

PCT Pub. Date: May 6, 2005

(65) Prior Publication Data

US 2009/0099338 A1 Apr. 16, 2009

(30) Foreign Application Priority Data

Oct. 24, 2003 (JP) .............................. 2003-365178
Mar. 29, 2004 (JP) .............................. 2004-096216

(51) Int. Cl.
*C12P 21/06* (2006.01)
*C12N 15/70* (2006.01)
*C12N 15/00* (2006.01)

(52) U.S. Cl. .................... 435/69.1; 435/320.1; 435/358
(58) Field of Classification Search ................ 435/69.1, 435/320.1, 358
See application file for complete search history.

(56) References Cited

U.S. PATENT DOCUMENTS 6,187,588 B1 * 2/2001 Hui et al. .................... 435/455

FOREIGN PATENT DOCUMENTS

WO 01/23592 A2 4/2001

OTHER PUBLICATIONS

Lin, G. et al., Stable cell lines expressing baculovirus P35: resistance to apoptosis and nutrient stress, and increased glycoprotein secretion, In Vitro Cell Dev.Biol.Anim., 2001, vol. 37, No. 5, pp. 293-302.
Greenberg, C.S. et al., "Cleavage of blood coagulation factor XIII and fibrinogen by thrombin during in vitro clotting," J. Clin. Invest., 1985, vol. 75, No. 5, pp. 1463-1470.
Roy, S.N. et al., "Assembly and secretion of recombinant human fibrinogen," J. Biol. Chem., 1991, vol. 266, No. 8, pp. 4758 to 4763.
Morita, T. et al., "Purification and properties of prothrombin activator from the venom of *Echis carinatus*," J. Biochem. 1978, vol. 83., No. 2, pp. 559 to 570.

* cited by examiner

*Primary Examiner*—Maryam Monshipouri
(74) *Attorney, Agent, or Firm*—Browdy and Neimark, PLLC

(57) ABSTRACT

A gene encoding a production amount-potentiating factor is introduced into an animal cell to transform the cell. Alternatively, a protein production gene and the gene encoding the production amount-potentiating factor are introduced into the animal cell to transform the cell. Herein, as the production amount potentiating factor, there is used a factor having caspase activity inhibiting activity and/or protein biosynthesis activity potentiating action, for example, baculovirus P35. Further, the animal cell is cultured by a culturing method under a condition that apoptosis is not induced, so that a protein is mass-produced.

16 Claims, 6 Drawing Sheets

Fig. 1
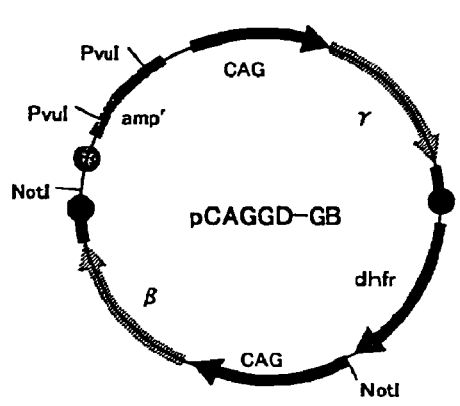
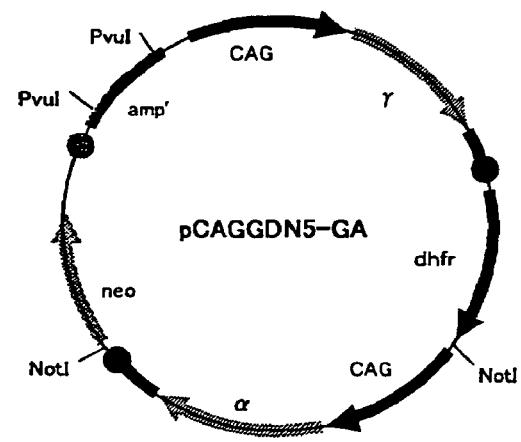

Fig. 3
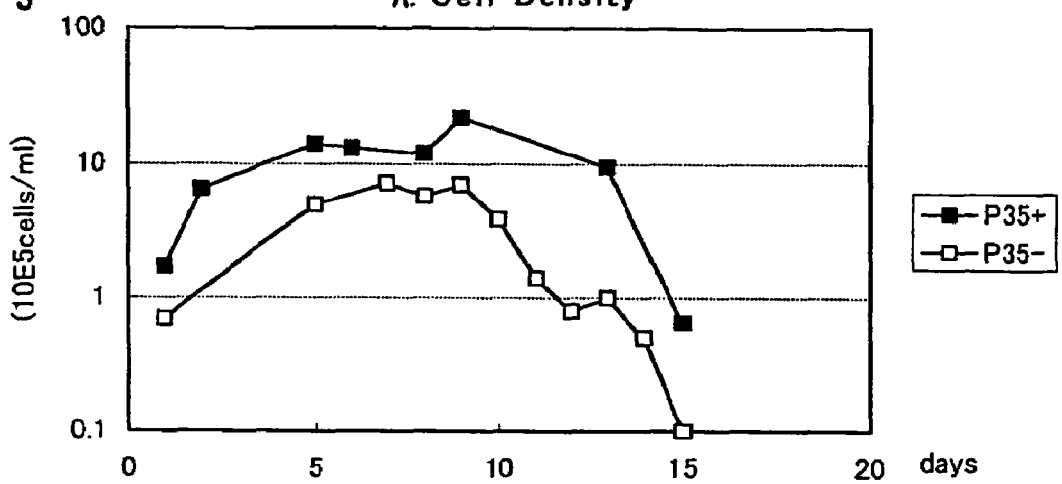
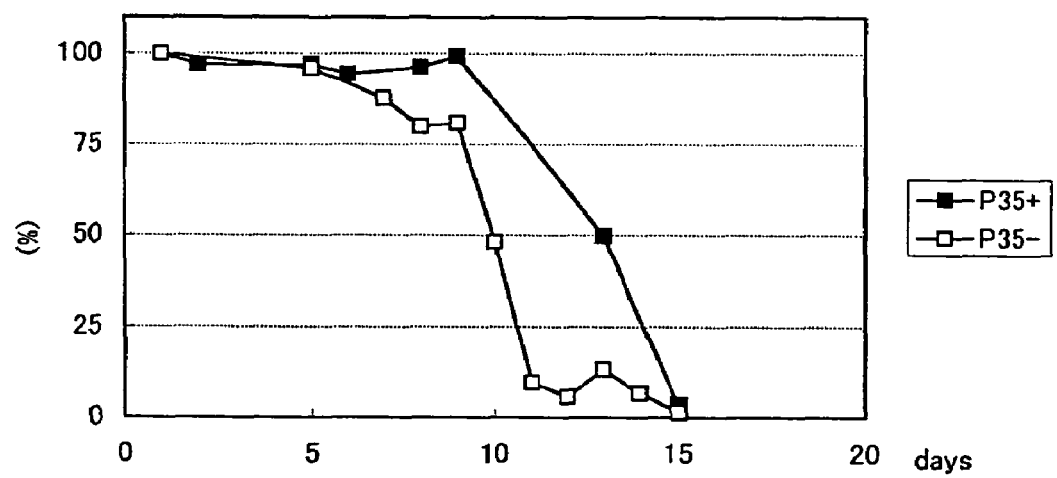
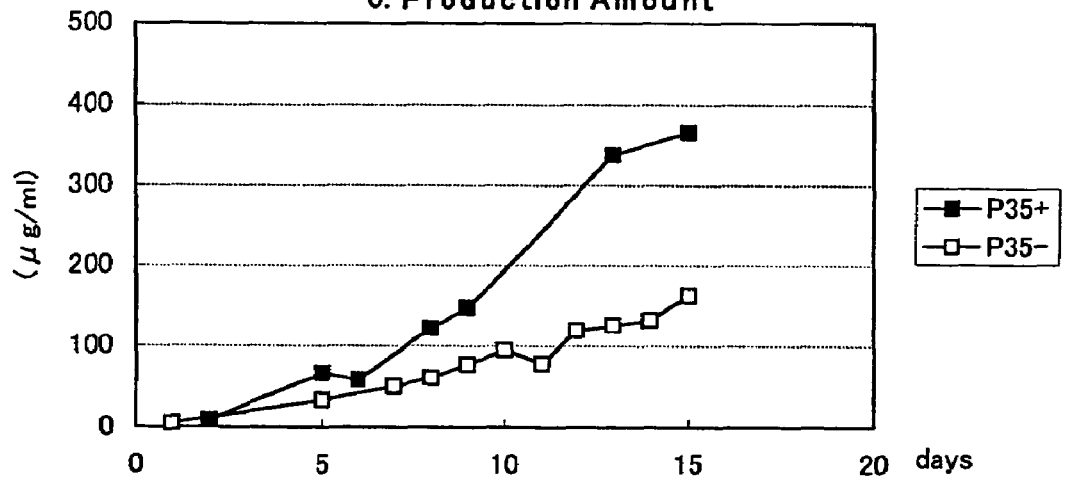

Fig. 6
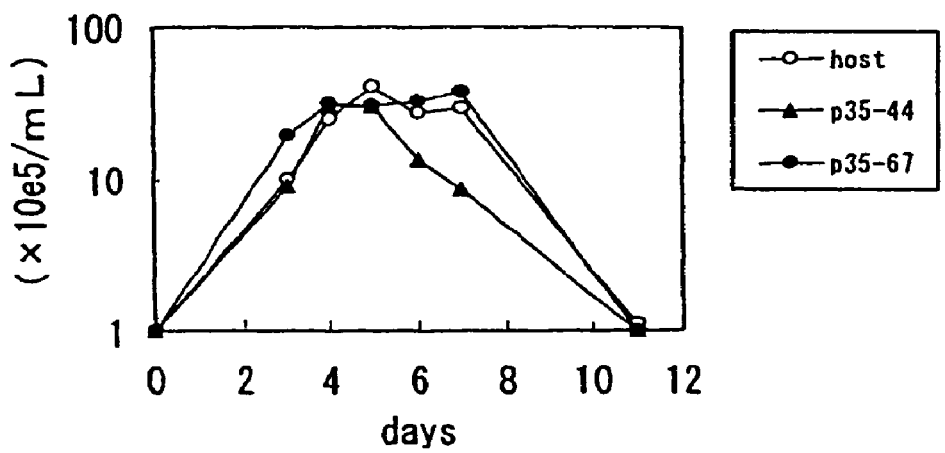
A. Cell Density
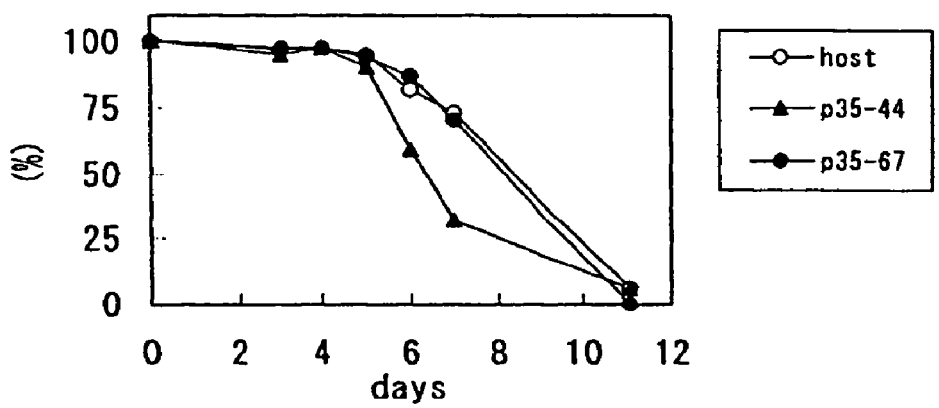
B. Viability
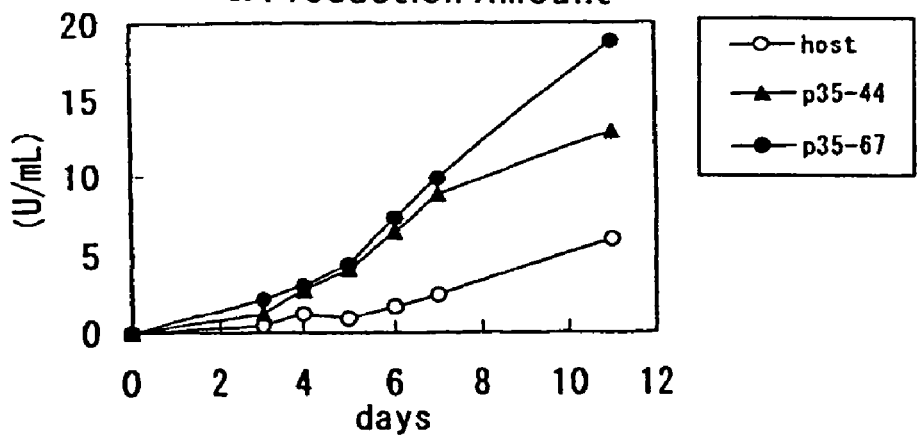
C. Production Amount

PROTEIN HIGHLY PRODUCING RECOMBINANT ANIMAL CELL, METHOD FOR PREPARING THE SAME, AND METHOD FOR MASS-PRODUCING PROTEIN USING THE SAME This is a 371 National Stage application of International application no. PCT/JP2004/015594, filed Oct. 21, 2004, which claims priority to Japanese patent application no. 2004-96216, filed Mar. 29, 2004, and Japanese patent application no. 2003-366178, filed Oct. 24, 2003. The entire contents of the above-referenced applications are hereby incorporated by reference in their entirety.

TECHNICAL FIELD

The present invention relates to a method for preparing a protein highly producing recombinant animal cell, and a method for mass-producing a protein-biosynthesis active protein using the same. More specifically, the present invention relates to a method for introducing, into an animal cell, a gene of a factor increasing protein biosynthesis activity, a representative of which is baculovirus P35 and/or a gene of a factor having anti-apoptosis activity, inter alia, a gene of a factor directly inhibiting caspase activity to thereby preparing a recombinant animal cell mass-producing an objective protein, and expressing the gene to thereby increase the production amount of the objective protein.

BACKGROUND ART

In recent years, a protein which can be utilized in medicaments has been extensively tried with the use of the gene recombinant technique. Since a protein having a great molecular size, various modifications such as addition of a sugar chain, and a protein of a subunit structure consisting of a plurality of polypeptide chains can not be responded in an expression system using microorganisms such as yeast and *Escherichia coli* as a host, a production system using animal cells as a host is used in many cases. Such a protein is produced using a mammal cell among the animal cells, in many cases. In the case where the protein is a secretion protein, since an objective protein is recovered in the culture supernatant, generally, a method for culturing a recombinant animal cell in a suitable medium, culturing the cell for a constant term and, thereafter, recovering the culture supernatant collectively (batch culturing), or a method for continuously performing extraction and addition of a suitable amount of a medium at an arbitrary time (perfusion culturing) is used. In any event, as the number of recombinant animal cells producing the objective secretion protein is increased, an accumulation (production) amount of a secretion protein in a culture is increased. Proliferation of a cell is classified into three terms of a logarithmic phase in which a cell is logarithmically proliferated, a stationary phase in which the number of cells is apparently constant, and a death phase in which cells die and the number of cells is decreased. In order to increase the production of the secretion protein, it is important to increase the cell density of the recombinant animal cell in the stationary phase as high as possible, and maintain the term as long as possible. Particularly, in the case of batch culturing, the recombinant animal cell is proliferated in the constant amount of the medium. Therefore, in order to increase the production amount of the secretion protein therein, various attempts have been tried to increase the cell density at the stationary phase as high as possible, and maintain the term as long as possible.

As an attempt to maintain the stationary phase long, from a viewpoint of growing, there has been adopted a method for improving the proliferating property to extend the stationary phase by devising a nutrient component such as improvement in a medium component and addition of a growth factor. In addition, as a culturing method, there is a method for extending the stationary phase long by supplementing a nutrient to a cell at the stationary phase at a suitable interval, to prevent nutrient depletion, such as a fed batch culturing method. A perfusion method is a method for performing this continuously. In order to increase the production amount of the objective protein, usually, such a growing method has been adopted. As a method which is different from the growing method, an attempt has also been tried to improve a host cell. For example, there has been tried a method for using an anti-apoptotic factor. This method is an attempt to express an anti-apoptotic factor gene in a recombinant animal cell producing a protein, imparting to the cell the ability of suppressing programmed cell death (apoptosis) generated by nutrient starvation, thereby extending the stationary phase.

According to Non-Patent Document 1, a mechanism for causing apoptosis is considered as follows. When a variety of cell death stimulations such as nutrient depletion are transmitted to a cell, the signal is transmitted to mitochondrion via various proteins including a transcription factor and a kinase. A mitochondrion having received the signal releases an apoptosis signal transmitting factor (AIF, cytochrome c etc.) into a cytoplasm. Cytochrome c binds to Apaf-1 (apoptosis activating factor-1) and pro-caspase-9 present in the cytoplasm to form a complex, and activates caspase-9. An activated caspase cascade cuts various intracellular or intranuclear substrates to induce a variety of morphological or biochemical changes (actin degradation, DNA fragmentation, chromosome condensation etc.) characteristic in apoptosis. As a factor suppressing such apoptosis, Bcl-2 (B cell lymphoma/leukemia 2) is well-known. The Bcl-2 gene was found as an oncogene which is seen in human follicular lymphoma at a high frequency. Currently, many family genes having a domain (BH1-4) having high homology with Bcl-2 are identified. In a family, there are a factor serving suppressively on apoptosis, and a factor serving promotively on apoptosis. As the suppressive factor, for example, Bcl-xL, Bcl-w, Mcl-1, A1, BHRF1, E1B-19K and Ced-9 are known, and it is thought that they inhibit signal transmission by inhibition of the aforementioned release of cytochrome c, or binding with Apaf-1 and procaspase-9. It is thought that the suppressive Bcl-2 family functions upstream of a caspase cascade.

On the other hand, there is also known a factor which acts downstream of the caspase cascade (inhibits the directly activity of the caspase) to exhibit the cell death suppressing effect. For example, a p35 protein of AcNPV (Autographa californica nuclear polyhedrosis virus) belonging to a baculovirus family is cut as a substrate for caspase and, the fragment forms a stable complex with almost all caspases, so that activity thereof is inhibited. Therefore, various apoptosis can be suppressed. BmNPV (Bombyx mori nuclear polyhedrosis virus) closely-related to AcNPV also has a p35 gene. In addition, crmA of cowpox virus specifically binds to caspase-1-like protease or caspase-8,-10 to inhibit this, so that apoptosis can be suppressed. In addition, v-FLIP derived from herpesvirus has two DEDs (death effecter domains), and binds to an FADD (Fas-associating Protein with death domain), so that activation of caspase-8 is suppressed. Further, in many closely-related viruses including CpGV (Cidia pomonella granulosis virus) and OpMNPV (Orgyia pseudotsugata multinucleocapsid nucleopolyhedrovirus) of a baculovirus family, a v-IAP (inhibitor of apoptosis) gene, the expression product of which directly inhibits caspase activity, has been identified, different from a p35 gene. Up to now, as a homologue of v-IAP, an IAP family having several kinds of BIRs (baculovirus IAP repeats) such as c-IAP1/hia-2, c-IAP2/hia-1, XIAP, NAIP, survivin, TIAP, Apollon, DIAP1, DIAP2, SfIAP and ITA has been identified in *Drosophila* and a mammal in addition to a virus.

An attempt has been tried to utilize the factor having anti-apoptosis activity, for example, a Bcl-2 family in cell culturing, but now, the effect on enhancement of a production amount of a protein has not been revealed regarding a Bcl-2 family. For example, when a Bcl-2 gene is introduced into a CHO cell producing a chimera antibody to express it, Tey B T et al. observed the viability extending effect, but an antibody production amount was not changed (see Non-Patent Document 2). Simpson N H et al. introduced a Bcl-2 gene into a hybridoma, but this did not also lead to increase in the antibody producing ability (see Non-Patent Document 3). Similarly, Kim N S, Lee G M et al. reported that, in an antibody-producing CHO cell in which a Bcl-2 gene is expressed in batch culturing, little change is recognized in an antibody production amount as compared with the case where the gene is not expressed (see Non-Patent Documents 4 and 5). On the other hand, they increased an antibody production amount by suppression of apoptosis inducing action possessed by butyric acid by Bcl-2 when sodium butyrate is added simultaneously and, consequently, enhancement of production amount potentiating action possessed by butyric acid (see Non-Patent Document 5).

In addition, they found out that, similarly, expression of Bcl-2 suppresses cell death due to a high osmotic pressure, and reported that a production amount can be increased by assisting antibody production potentiating effect due to a high osmotic pressure (see Non-Patent Document 6). These reports that, even when Bcl-2 exerts cell death suppressing effect, this is not directly involved in the effect of potentiating a production amount of a secretion protein such as an antibody. In addition, it was reported that expression of Bcl-2, Bcl-xL or E1B-19K acts towards reduction in cell proliferation (see Non-Patent Document 7). Similarly, MCL-1 which is a Bcl-2 family also improves in viability of a cell, but it does not influence on a signal of cell proliferation (see Non-Patent Document 8). Bcl-xL also improves cell viability, but there is a report that it does not contribute to improvement in a production amount of a secretion protein. For example, in a transgenic mouse in which a gene expressing Bcl-xL under control of an insulin promoter was introduced, Bcl-xL improved viability of a β cell, but decreased secretion expression of insulin due to glucose inducement rather than potentiated it (see Non-Patent Document 9). Similarly, when production of inflammatory cytokine such as TNFα due to LPS inducement was examined using a RAW264 macrophage cell in which Bcl-xL was expressed, a production amount was decreased (see Non-Patent Document 10). An E1B-19K gene which is similarly a Bcl-2 family was introduced into antibody-producing NS/O myeloma, but improvement in a production amount was not recognized (see Non-Patent Document 11).

Like this, although all of the methods using an anti-apoptotic factor derived from a Bcl-2 family such as Bcl-2, Bcl-xL and E1B-19K which have previously been tried can suppress cell death, and extend a stationary phase of a proliferation curve, a production amount is not increased as expected, in many cases. From these things, it is thought that the direct effect of potentiating a production amount of a protein is not present in these factors, or if any, the effect is exerted under the especial environment. On the other hand, regarding a factor having caspase inhibiting action, a representative of which is P35 of baculovirus, there is no report that a relationship with the production amount potentiating effect was investigated in a recombinant protein producing cell, much less, there is no report that there is the production amount potentiating effect in a recombinant secretion protein producing cell.

In the present invention, fibrinogen, ecarin and factor VIII are used as one example of a protein which is a subject of the present invention. Fibrinogen as one of blood coagulation factors plays a role in coagulating blood when a living body undergoes injury. The first function is to form a body of a thrombus called fibrin clot at an injured site, and the second function is to serve as an adhesive protein necessary for platelet aggregation. A blood concentration of fibrinogen is usually about 3 mg/ml, and this is the third highest next to albumin and immunoglobulin G. Fibrinogen is a macro glycoprotein consisting of a total six of polypeptides having each two of three different kinds of polypeptides called an α chain, a β chain and a γ chain. Individual molecular weights of polypeptides are such that the α chain has about 67000, the β chain has about 56000 and the γ chain has about 47500, and a molecular weight of fibrinogen which is an aggregate of them mounts to about 340000 (see Non-Patent Document 12). In fibrinogen in blood, there are heterogenous molecules due to existence of heterogenous polypeptides having different molecular sizes. For example, the existence of a heterogenous type called γ chain (or γB chain) in a γ chain has been reported, and it has been revealed that this is a polypeptide consisting of a total 427 of amino acid residues in which 20 amino acid residues are added to a 408-position of an amino acid sequence of the γ chain (see Non-Patent Document 13). In addition, there is a heterogenous type called αE is present also in the α chain, and it has been reported that this polypeptide has a total 847 of amino acid residues in which 236 amino acid residues are extended to a 612-position of an amino acid sequence of the α chain (see Non-Patent Document 14).

A fibrinogen preparation is effective in inhibiting severe bleeding by enhancing a fibrinogen concentration in blood by a method such as intravenous administration, and is used in improving the consumption state of a blood coagulation factor, for example, such as disseminated intravascular coagulation (DIC) in sepsis, or in replenishing therapy in congenital or acquired fibrinogen efficiency.

In addition, the fibrinogen preparation is also widely utilized as a tissue adhesive utilizing adherence of fibrin (see Non-Patent Document 15). This living body-derived adhesive utilizes gelation of fibrinogen in a living body, and is widely used in hemostasis, closure of a wound site, adhesion or suture reinforcement of a tissue such as nerve, tendon or vessel, and closure of air leakage in lung. In addition, in recent years, a preparation having enhanced convenience by attaching fibrinogen to a sheet of collagen etc. has been commercially available.

Currently, fibrinogen used as a medicament is prepared from human plasma, and examples of a problem thereof include 1) a risk of mixing in of an infective pathogen such as a virus causing pneumonia such as HAV, HBV, HCV, HEV and TTV, a virus causing immunodeficiency such as HIV, and abnormal prion causing CJD because of use of plasma collected from unspecified many humans, and 2) supply of plasma by blood donation in Japan and, consequently, a problem of stable supply in the future.

In order to overcome these problems, recombination of fibrinogen has previously been tried. For example, in *Escherichia coli*, a fibrinogen γ chain was successfully expressed in a bacterium, but there is no report that a functional fibrinogen molecule is produced by simultaneously expressing three proteins of an α chain, a β chain and a γ chain. In addition, also in an expression system using yeast, there was a report that secretion expression was successful at a certain time, but reproductivity was not finally confirmed, and the report was withdrawn (see Non-Patent Document 16). Like this, there has not been yet a report that fibrinogen was successfully expressed using *Escherichia coli* or yeast.

On the other hand, ecarin is a snake venom-derived protease which has been isolated and purified from Echis carinatus (Non-Patent Document 17), and is known to specifically convert prothrombin playing an important role in blood coagulation into activated thrombin. Thrombin used as a medicament is used as a hemostatic agent. It is used in bleeding from a small vessel, a capillary vessel and a parenchymal internal organ for which hemostasis is difficult by conventional ligation (e.g., bleeding accompanied with trauma, bleeding during operation, bone bleeding, bladder bleeding, bleeding after tooth extraction, nose bleeding, and bleeding from an upper digestive tract such as gastric ulcer). A current thrombin preparation is derived from bovine blood, or prepared from human plasma and, as a problem thereof, the preparation has the same problems as those of fibrinogen, such as 1) a risk of mixing in of an infective pathogen, and 2) stable supply in the future and, thus, thrombin obtained by the recombinant technique is desired. Upon preparation of such thrombin, it is difficult to produce thrombin as activated thrombin from the beginning, and it is necessary to produce prothrombin and, thereafter, activate the prothrombin using any enzyme. As an effective converting enzyme, ecarin is mentioned as a candidate, but ecarin is also derived from snake venom, has a problem of its supply and mixing in of an infective pathogen and, thus, recombination has been desired. In addition, since ecarin acts also on abnormal prothrombin biosynthesized in the absence of vitamin K, it is utilized in measuring a blood concentration of the abnormal prothrombin. However, only a small amount is purified from a snake venom, and it can not be used as a general reagent. That is, it is essential in a step of preparing a thrombin preparation made by the recombination technique to supply ecarin obtained by the recombination technique at a large amount and, also as a clinical diagnostic, high production has previously been desired for practical use of ecarin.

Factor VIII is an important coagulation factor which amplifies a reaction of activating factor X by activated factor IX about 200 thousands-fold in a blood coagulation reaction. When the factor VIII is deficient, there is a tendency of serious bleeding, and this is known as hemophilia A. Hemophilia A is a congenital bleeding disease based on deficiency in a blood coagulation factor VIII, is usually developed in a man, and an incidence rate is said to be one per 5000 to 10000 of male birth. A bleeding symptom begins at an infant stage and thereafter in many cases, and generally appears subcutaneously, intra-articularly, intramuscularly, hematurically, orally, or intracranially. When intra-articular bleeding is repeated, a joint disorder progresses, leading to chronic hemophilic arthrosis accompanied with limited movement of a joint. Therapy of hemophilia A is an intravenous injection of a factor VIII preparation in principle. Currently, both of a blood-derived factor VIII preparation and a recombinant preparation are commercially available, and a blood-derived preparation has a problem of a risk of mixing in of an infective pathogen and stable supply as described above. On the other hand, regarding a recombinant preparation, products are lacked, and supply becomes deficient, causing a social problem. For solving these problems, high production necessary for increasing production of the recombinant preparation has been desired.

In the case of fibrinogen, in an animal cell, expression has been tried using a BHK cell (see Non-Patent Document 18), a COS cell (see Non-Patent Document 19), or a CHO cell (see Non-Patent Documents 20, 21 and 22, and Patent Document 1), but the production amount is only around 1 to 15 μg/ml. In these cases, any of a metallothionein promoter a Rous sarcoma virus LTR promoter, and an adenovirus 2 major late promoter is used and, as a selectable marker, any of an aminoglycoside 3' phosphotransferase (neo) gene, a dihydrofolate reductase (dhfr) gene and a histidinol resistant gene, or a combination thereof is used. In any case, a method for independently constructing each of expression vectors of genes each encoding an α chain, a β chain or a γ chain, transfecting a cell with three of them simultaneously, or transforming a cell with each two expression vectors having an α chain gene, a γ chain gene or a β chain gene and a γ chain gene in advance and, thereafter, introducing an expression vector having a β chain gene and an α chain gene, or a method for mixing an equal amount of a plasmid having an α chain gene and a γ chain gene and a plasmid having a β chain gene, and introducing the mixture into a cell is adopted. In any case, there is no particular description regarding a constitutional ratio of the respective genes upon introduction, and it is presumed that an equal amount of the respective genes are introduced as in the conventional procedure. In a medicament using blood-derived fibrinogen which is currently used, for example, in the case of a fibrin paste preparation, about 80 mg/dose of fibrinogen is used, and a manufacturing facility must be unavoidably scaled up at an expression amount of around ten and a few μg/ml as described above, and this inevitably leads to the high cost. For preparing fibrinogen at a practical level by the gene recombination technique, a highly producing cell (e.g., an expression amount of fibrinogen is 100 μg/ml or more) is necessary, but currently, there is no report of an expression system using a recombinant animal cell satisfying this.

Patent Document 1: U.S. Pat. No. 6,037,457
Non-Patent Document 1: "Apoptosis and Disease, Chapter; Central Nervous System Disease" edited by Yoshikuni Mizuno, Medicine and Drug Journal (2000)
Non-Patent Document 2: Tey B T et al., Biotechnol. Bioeng., 68, 31 (2000)
Non-Patent Document 3: Simpson N H et al., Biotechnol. Bioeng., 64, 174 (1999)
Non-Patent Document 4: Kim N S and Lee G M, Biotechnol. Bioeng., 82, 872 (2003)
Non-Patent Document 5: Kim N S and Lee G M, Biotechnol. Bioeng., 71, 184 (2000/2001)
Non-Patent Document 6: Kim N S and Lee G M, J. Biotechnol., 95, 237 (2002)
Non-Patent Document 7: O'Reilly L A et al., EMBO J., 15, 6979 (1996)
Non-Patent Document 8: Yang T et al., J Cell Physiol., 166, 523 (1996)
Non-Patent Document 9: Zhou Y et al., Am. J. Physiol. Endocrinol. Metab., 278, E340 (2000)
Non-Patent Document 10: Lakics V et al., J. Immuno., 165, 2729 (2000)
Non-Patent Document 11: Mercille S et al., Biotechnol. Bioeng., 63, 516 (1999)
Non-Patent Document 12: "Hemostasis, Thrombus, Fibrinogenolysis" edited by Matsuda and Suzuki, Chugai Igakusha (1994)

Non-Patent Document 13: Chung D E and Davie E W, Biochemistry, 23, 4232 (1984)
Non-Patent Document 14: Lawrence Y F et al., Biochemistry, 31, 11968 (1992)
Non-Patent Document 15: "Special Edition; Bioadhesive" Biomedical Perspectives, 6, 9-72 (1997)
Non-Patent Document 16: Redman C M and Kudryk B, J. Biol. Chem., 274, 554 (1999)
Non-Patent Document 17: T. Morita et al.: J. Biochemistry, 83, 559-570, (1978)
Non-Patent Document 18: Farrell D H et al., Biochemistry, 30, 9414 (1991)
Non-Patent Document 19: Roy S N et al., J. Biol. Chem., 266, 4758 (1991)
Non-Patent Document 20: Lord S T et al., Blood Coagul Fibrinolysis, 4, 55 (1993)
Non-Patent Document 21: Binnie C G et al., Biochemistry, 32, 107 (1993)
Non-Patent Document 22: Lord S T et al., Biochemistry. 35, 2342 (1996)

DISCLOSURE OF THE INVENTION

Problems to be Solved by the Invention

As described above, in culturing of a recombinant animal cell producing a protein, particularly, a secretion protein, how a cell density is increased for increasing a production amount, and how a stationary phase of a proliferation curve is maintained long were a problem. However, under the current circumstances, effective solving strategy has not been found out other than a growing method such as a method for adding a depleted nutrient factor to extend a stationary phase such as fed batch culturing, or a method for improving the nutrient condition such as addition of an amino acid or a growth factor to enhance the proliferation property of a cell, thereby increasing a cell density. Therefore, a new method of improving and reforming the cell culturing condition which can be replaced for the growing method, or can be used jointly with the growing method has been desired.

Therefore, an object of the present invention is to provide a method for improving and reforming the culturing condition for a recombinant animal cell producing a protein, particularly, a secretion protein in addition to the growing method.

Another object of the present invention is to provide a recombinant animal cell highly producing the protein, particularly, the secretion protein obtained by the method, as well as the protein obtained by the method.

Means for Solving the Problems

In order to accomplish the aforementioned objects, the present inventors intensively continued to study and, as a result, found out that, by expressing a gene encoding a factor having the action of increasing protein biosynthesis activity and/or anti-apoptosis activity, inter alia, a gene encoding a factor having the action of inhibiting caspase activity, desirably, a baculovirus P35 gene in a recombinant animal cell producing a protein using fibrinogen, ecarin and factor VIII which were difficult to be mass-produced by the previous technique as one example of a protein to be produced, the effect of potentiating the protein producing ability which has not previously been seen, which resulted in completion of the present invention. Further, the present inventors have revealed that this potentiation of the production amount has two cases of the case where this factor contributes to potentiation of protein biosynthesizing activity as a factor for potentiating the production amount, and the case where the factor contributes to apoptosis activity inhibition and, in the former case, since the potentiation of the production amount is obtained before term of apoptosis occurrence, it was found to be very high in industrial utilization value without selecting a medium.

Therefore, the present invention encompasses a method for preparing a recombinant animal cell comprising a step of transforming an animal cell using a gene encoding a factor having the action of increasing protein biosynthesis activity and/or anti-apoptosis activity, inter alia, a gene encoding a factor having the action of inhibiting caspase activity, desirably, a baculovirus P35 gene.

The present invention also encompasses a recombinant protein producing cell which highly expresses a protein obtained by the aforementioned method, and a protein obtained by the cell.

Effects of the Invention

An animal cell highly producing an objective protein which was prepared by the method of the present invention is recognized to have the cell proliferating ability, and the effect of potentiating a production mount per cell in addition to extension of a term of a stationary phase in cell proliferation, and the ability other than the effect of extending viability which has previously been reported in Bcl-2 can be acquired. The effect was investigated using a fibrinogen-producing cell and baculovirus P35 as one example and, as a result, a production amount of fibrinogen in accordance with the conventional technique was maximally about 15 µg/ml, while in the case where a P35 gene is introduced in accordance with the present invention, the effect of potentiating the production amount which is about 42-fold that of a spinner culturing level was obtained. In addition, in the case where the P35 gene is introduced, it is presumed that a potential production amount of about 704 to 3952 µg/ml is possessed by simple calculation. Like this, according to the method of the present invention, there can be obtained a recombinant animal cell which highly produces an objective protein which has never been seen.

It has been thought that the conventional production potentiating effect by apoptosis suppressing activity is exerted best even when cultured under the condition for inducing apoptosis in a protein-producing cell such as a culturing later stage where the nutrient state becomes worse, and culturing with a drug exhibiting expression potentiating activity at a concentration region showing cell toxicity such as butyric acid, or any factor exhibiting cytotoxicity. The present invention exerts the effect also in culturing not under such the special condition, but under the general culturing condition, that is, at a normal term at which viability is not reduced. This point is clearly different from the conventional potentiation of the production amount by the apoptosis suppressing factor. The present invention can be also used jointly with the existing growing method such as fed batch culturing and perfusion culturing, and the protein producing ability of a recombinant animal cell can be further potentiated. Therefore, the present invention enables considerable cost down by further potentiation of a production amount not only in commercialization of a protein which has previously been low in productivity in an animal cell, and difficult to be industrialized, but also protein production which has been also commercialized.

Also in the recombinant human fibrinogen producing cell, the ecarin producing cell or the factor VIII producing cell shown as one example of the present invention, the present invention first enables establishment of a method for preparing human fibrinogen, ecarin or factor VIII at a practical level and, by establishment of the method, stable supply of fibrinogen, ecarin or factor VIII to the market is maintained. In addition, when the recombinant human fibrinogen producing cell, the ecarin producing cell, or the factor VIII producing cell obtained by the method of the present invention, mixing in of an infective pathogen which has been previously feared when produced using blood as a raw material, and involvement of other blood-derived components can be excluded, and it becomes possible to produce and supply a safer blood preparation.

BRIEF DESCRIPTION OF THE DRAWINGS

FIG. 1 shows an expression vector for preparing a recombinant fibrinogen producing cell.

FIG. 3 A-C respectively, show a change with time in a cell density, viability and a fibrinogen production amount in spinner culturing of a cell expressing a baculovirus P35 gene and a cell not expressing the gene.

FIG. 6 A-C respectively, show a change with time in a cell density, viability and an ecarin production amount in spinner culturing of a cell expressing a baculovirus P35 gene and a cell not expressing the gene.

BEST MODE FOR CARRYING OUT THE INVENTION

Figure 2:
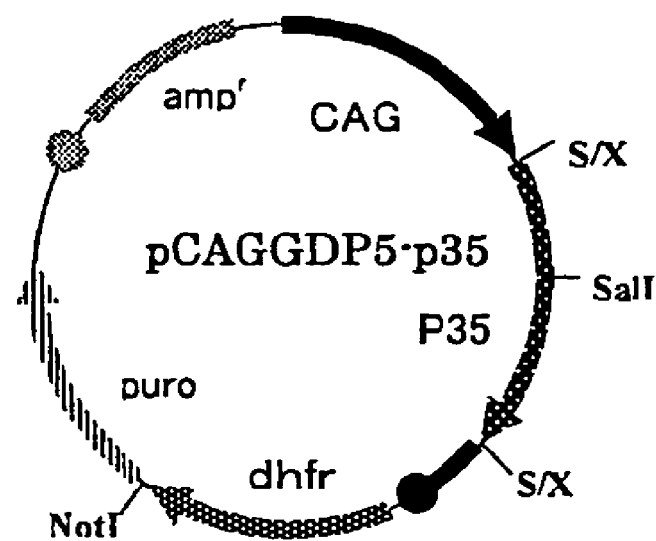
FIG. 2 shows an expression vector for preparing a baculovirus P35 gene expressing cell.

The method of the present invention is characterized by a method using a recombinant animal cell highly producing a protein, the method comprising a step of expressing a gene encoding a factor having the action of allowing a host animal cell producing a protein to increase protein biosynthesis activity and/or anti-apoptosis activity, inter alia, a gene encoding a factor having the action of directly inhibiting caspase activity, for example, a baculovirus P35 gene in a recombinant animal cell producing a protein.

Examples of the factor having action of increasing protein biosynthesis activity and/or action of inhibiting caspase include factors derived from a virus such as a baculovirus (AcNPV or BmNPV) P35 gene, a cowpoxvirus crmA gene, a herpesvirus-derived v-FLIP gene, a baculovirus v-IAP gene, an adenovirus Ad14.7 gene, and other viral factors having homology with baculovirus-derived v-IAP. Other examples include those derived from a virus such as an IAP family with BIR (baculovirus IAP repeat) derived from an animal cell having homology with baculovirus-derived v-IAP. Examples of such a factor include c-IAP1/hia-2, c-IAP2/hia-1, XIAP, NAIP, survivin, TIAP, Apollon, DIAP1, DIAP2, Sf1AP, and ITA which were found out in *Drosophila* and mammals. These factors may be applied to the present invention as far as they are factors obtained by gene expression such as a peptidic suppressing factor, and a protein suppressing factor. Among these factors, one example of a most preferable factor is a P35 gene of baculovirus AcNPV.

As a protein which is a subject of potentiation of a production amount, any protein can be a subject as far as it is a protein which can be expressed by introducing a gene in various host animal cells, and a subject is desirably a protein, a production amount of which is increased with proliferation of a host cell. Further, among such proteins, a secretion protein whose expression product can be recovered in a culture supernatant is a most desirable subject protein. Examples of such a protein include antibodies, cytokines, growth factors, hormones, plasma proteins, enzymes, receptors, ligands, metabolites, viruses, and viral proteins. In the present invention, as one example of the protein, fibrinogen, ecarin and factor VIII derived from a human are handled, but the protein is not limited to them, and other method for preparing a protein-producing cell may be used.

As genes encoding polypeptides constituting human fibrinogen used as one example in the present invention, an α chain, a β chain and a γ chain, any of cDNA and a chromosomal gene can be used as far as it is a gene whose expression product can be finally assembled to form a human fibrinogen molecule. As described above, in the α chain and the γ chain, there are heterogeneous types called an αE chain and a γ (γB) chain, respectively. In addition to them, genes encoding other heterogeneous polypeptides which may be newly found out from now on can be similarly used in the present invention.

The aforementioned desired genes can be cloned by a conventional PCR method by obtaining nucleic acid nucleotide sequences by utilizing literatures describing a nucleic acid nucleotide sequence of each gene, or the existing gene database such as GENBANK, designing a PCR primer based on the sequences, and using, as a template, a DNA derived from an RNA, a DNA or a mRNA of a cell, a tissue or a virus which is to be a suitable gene source. The desired gene can be obtained by designing a PCR primer based on a sequence reported in the literature (Friesen, P. D. and Miller, L. K., J. Viral. 61, 2264-2272 (1987)) in the case of the baculovirus P35 gene, a sequence reported in the literature of Nishida et al., (Biochemistry, 34, 1771, 1995) in the case of the ecarin, a sequence reported in the literature of J. Gitschier et al. (Nature, 312, 326, 1984) in the case of the factor VIII, or a sequence reported in the literature (Rixon M W et al., Biochemistry, 22, 3237 (1983), Chung D W et al., Biochemistry, 22, 3244 (1983), Chung D W et al., Biochemistry, 22, 3250 (1983), see Non-Patent Documents 13 and 14) in the case of the fibrinogen gene, and performing PCR using, as a template, a baculovirus-infected cell or a viral genome in the former case, or using, as a template, a cDNA derived from a snake poison gland in the case of the ecarin, or a cDNA derived from an internal organ or a cell producing factor VIII or fibrinogen such as human liver in the latter two cases.

More specifically, a virus genome DNA or RNA can be generally prepared by the following method. When a is extracted from a virus-infected cell, protein components are degraded by adding 10-fold or more of a solubilizing buffer containing SDS and proteinase K (one example of composition: 150 mM-NaCl, 10 mM-Trais-HCl pH 8.0, 10 mM-EDTA, 0.1%-SDS, proteinase K100 μg/ml) to a cell sediment, and mildly shaking this at 37° C. for several hours to overnight. Thereafter, according to a conventional procedure of DNA extraction, a DNA is recovered by phenol treatment, and ethanol precipitation (Hiroki Nakanishi and Takahito Nishikata, Bio-Experiment Illustrated volume 2, P117-123, 1997, Shujunsha). On the other hand, when a DNA or an RNA is extracted from a viral particle, a method of first concentrating a viral particle from a culture supernatant or a cavity liquid of a grown chicken egg used in proliferation generally by ultracentrifugation is used. The condition of ultracentrifugation is slightly different depending on a virus, and a method of purifying main viruses is described in a virus experimental protocol (supervised by Yoshiyuki Nagai and Akira Ishihama, Medical View 1995). Regarding extraction of a nucleic acid from a purified virus particle, in the case of a DNA virus, it can be prepared according to a method of extraction from an infected cell. On the other hand, in the case of an RNA virus (and preparation of an RNA from a cell), various extraction kits are commercially available, and the RNA can be prepared according to a procedure attached to each kit. As one example, when Catrimox-14 RNA Isolation Kit RIK 2.11w of Takara Shuzo is used, an equivalent amount of Catrimox-14 is mixed in a solution containing an RNA virus, and this is centrifuged for 5 minutes, and the RNA is recovered as a sediment. For example, in the case of the baculovirus P35 gene, a DNA which is used as a template of PCR can be prepared from a baculovirus-infected cell or a baculovirus solution by the aforementioned method.

Herein, cDNAs encoding an α chain, a μ chain and a γ chain of fibrinogen are prepared as follows. First, a total RNA is extracted from a human hepatocyte, and an mRNA is purified therefrom. The resulting mRNA is converted into a cDNA, a PCR reaction is performed using PCR primers designed in conformity with each gene sequence, and the resulting PCR product is incorporated into a plasmid vector, and introduced into *Escherichia coli*. A clone having a cDNA encoding an objective protein is selected from an *Escherichia coli* colony. Regents such as commercially available TRIzol regent (GIBCO BRL) and ISOGEN (Nippon Gene) are used for extracting the aforementioned total RNA, commercially available kits such as mRNA Purification Kit (Amersham BioSciences) are used for purifying the mRNA, and commercially available cDNA library preparing kits such as SuperScript plasmid system for cDNA synthesis and plasmid cloning (GIBCO BRL) are used for converting to the cDNA. When a human fibrinogen gene is obtained, a commercially available cDNA library, for example, Human Liver Marathon-Ready cDNA (BD Bioscience) is used.

A PCR primer is easily available when one requests synthesis undertaking organization (e.g., QIAGEN). Thereupon, it is desirable to add a KOZAK sequence for 5' (Kozak M, J. Mol. Biol., 196, 947 (1987)) and a sequence of a suitable restriction enzyme cutting site. Preferably, synthetic DNAs described in SEQ ID NOS: 1 to 6, 10, 11, 14 and 15 are used as a primer. The PCR reaction may be performed using commercially available Advantage HF-2 PCR Kit (BD Bioscience) according to an attached protocol. A nucleotide sequence of a DNA fragment obtained by PCR is cloned using a TA cloning kit (Invitrogen), and is determined with a DNA sequencer, for example, ABI PRISM310 Genetic Analyzer (PE Biosystems).

In this way, desired genes necessary for the present invention can be obtained. As one example thereof, the baculovirus P35 gene is obtained, preferably, as a gene fragment having a sequence described in SEQ ID NO: 12. The fibrinogen gene is obtained, preferably, as a gene fragment having sequences described in SEQ ID NOS: 7 to 9. In addition, the ecarin gene is obtained, preferably, as a gene fragment described in SEQ ID NO: 13, and the factor VIII is obtained, preferably, as a gene fragment described in SEQ ID NO: 16. Using these genes, an expression vector for incorporation into an animal cell is constructed. An expression vector using an animal cell as a host is not particularly limited, but a plasmid, a virus vector and the like can be used. As a promoter contained in the expression vector, any promoter can be used as far as it is a promoter by which a desired gene product is finally obtained, such as a SV40 initial promoter, a SV40 late promoter, a cytomegalovirus promoter, and a chicken β-actin promoter depending on a combination with a animal cell used as a host.

Alternatively, the promoter may be combined with a suitable enhancer. Preferably, a chicken β-actin promoter system expression plasmid, pCAGG (JP-A No. 3-168087) is used. Any can be used as far as it functions as a marker gene for selection or gene amplification. Generally, marker genes for selection or gene amplification which are generally known such as an aminoglycoside 3' phosphotransferase (neo) gene, a dihydrofolate reductase (dhfr) gene, a puromycin resistant enzyme gene, and a glutamine synthase (GS) gene (Kriegler M, supervised by Ikunosin Kato, Genetic Engineering for Laboratory Manual Animal Cell, Takara Shuzo (1994)) can be utilized.

A preferable example of an expression vector which is constructed by combining the aforementioned elements includes a vector shown in FIG. 2, in the case of the baculovirus P35 gene. In the case of the fibrinogen gene, examples include an expression vector having a gene encoding a γ chain and a β chain, and an expression vector having a gene encoding a γ chain and an α chain. More preferably, examples include pCAGGD-GB (having each one of genes encoding the γ chain and the β chain of fibrinogen, and having a dhfr gene as a selectable marker) and pCAGGDN5-GA (having each one of genes encoding the γ chain and the α chain of fibrinogen, and having the dhfr gene and a neo gene as a selectable marker) shown in FIG. 1. The three kinds of expression vectors are introduced into an animal cell. However, the present invention is not limited to these examples. Basically, the expression vector is not particularly limited as far as it is in a form that a gene encoding a factor having caspase activity inhibiting action, a representative of which is a baculovirus P35 gene having protein biosynthesis activity potentiating action, and an objective protein gene, a representative of which is three kinds of genes of an α chain, a β chain and a γ chain constituting ecarin, factor VIII or fibrinogen can be expressed simultaneously in the same cell. An introduction stage and an introduction order of the expression vector for the gene encoding the factor having caspase activity inhibiting action, a representative of which is the baculovirus P35 gene, and the expression vector for the objective protein gene, a representative of which is three kinds of genes of the α chain, the β chain and the γ chain constituting the ecarin, the factor VIII or the fibrinogen are not particularly limited. For example, an expression vector for a gene encoding a factor having protein biosynthesis activity potentiating action and an objective protein expression vector may be introduced in a host cell simultaneously or at separate times. When the expression vector for the gene encoding the factor having the protein biosynthesis activity potentiating action is introduced into the host cell in advance to obtain a new host cell, general utility is further increased. When the expression vector having the gene encoding the factor having the protein biosynthesis activity potentiating action and the expression vector having the objective protein gene are introduced into the host cell at separate times, it is necessary to use different selectable marker genes possessed by the respective expression vectors.

As the host cell into which the expression vectors are introduced, various animal cells such as a Chinese hamster ovary (CHO) cell, a mouse myeloma cell such as SP2/0, a BHK cell, a 293 cell, and a COS cell can be utilized, and a suitable cell may be selected depending on a promoter used in an expression vector, and a marker gene for selection and gene amplification. For example, in an expression vector constructed using a chicken β-actin promoter system expression plasmid, a BHK21 cell and a CHO cell DG44 strain are used.

When a host cell is transformed, the known method may be utilized. For example, a calcium phosphate method, a DEAE dextran method, a method of using a lipofectin system liposome, a protoplast polyethylene glycol fusing method, and an electroporation method can be utilized, and a suitable method may be selected depending on a host cell to be used (Molecular Cloning (3$^{rd}$ Ed.), Vol. 3, Cold Spring Harbor Laboratory Press (2001)).

For selecting and amplifying the transformed cell, a method which is performed generally at transformation of an animal cell may be used. For example, the cell after transformation is cultured at around 37° C. for about 10 to 14 days while a medium is appropriately exchanged using a selective medium obtained by adding methotrexate, G418, puromycin and the like in conformity with a selectable marker to be used, to a medium which is generally used in culturing an animal cell such as a serum-free medium such as a CHO-S-SFMII medium (GIBCO-BRL), an IS CHO-V medium (IS Japan), a YMM medium and the like, and a serum medium in which around 5 to 10% bovine fetal serum is added to an MEM alpha medium, an RPMI medium, or a Dulbecco's medium (all GIBCO-BRL). By this culturing, an untransformed cell dies, and only a transformed cell is grown. Further, on the transformed cell, selection and cloning of an objective protein producing cell strain are performed by a method such as a limiting dilution method. In a culturing method, various detecting methods can be used depending on a kind of a cell, and a nature of an objective protein. Generally, for detecting an objective protein or measuring an expression amount, a method which is used in detecting a protein or a polypeptide, that is, a method such as ELISA, RIA, WB, SDS-PAGE and the like may be utilized. In addition, when an objective protein retains any activity, the activity may be directly measured.

In the recombinant animal cell thus obtained, in addition to extension of a stationary phase in cell proliferation, the cell proliferating ability, and the effect of potentiating protein biosynthesis activity which potentiates a production amount per cell are recognized, and the cell can acquire the ability other than the effect of extending viability which has been reported in the conventional anti-apoptotic factor such as Bcl-2. Most importantly, it becomes possible to considerably increase the production amount of the objective protein, to such an extent that there has never been a report.

Further, in the present invention, even when cultured under such a condition that, among action possessed by a factor having caspase activity inhibiting activity and/or protein biosynthesis activity potentiating action to be used, apoptosis suppressing activity can not be exerted, that is, under the condition that apoptosis is not induced in a cultured cell, sufficient objective protein production potentiating effect is obtained. Examples of a culturing method under the condition that apoptosis suppressing activity can not be exerted include a perfusion culturing method in which a fresh medium is constantly supplied, a fed batch culturing method in which a fresh medium or a fresh nutrient component is appropriately added during culturing, and a culturing method using a medium which suppresses reduction in viability of a cell in late culturing by reinforcement of a nutrient component. In addition, in a conventional batch culturing, it becomes possible to potentiate a production amount without extending an alive term.

As one example, the effect of the fibrinogen producing cell or the factor VIII producing cell, the ecarin-producing cell and the baculovirus P35 was examined and, as a result, in the case of the fibrinogen, the production amount of the fibrinogen by the prior art was maximally about 15 µg/ml, but when a P35 gene was introduced in accordance with the present invention, about 42-fold production amount potentiating effect was obtained at a spinner culturing level. In addition, when the P35 gene is introduced, it is presumed that a potential production amount of about 704 to 3,952 µg/ml is possessed by simple calculation. In addition, in the ecarin production amount, 2.1 to 3.2-fold potentiating effect was recognized while the amount before was 5.96 U/ml in a cell before introduction. Also in the factor VIII-producing cell, 2.2 to 4.4-fold potentiating effect was recognized. By the method of the present invention, the effect of obtaining a recombinant animal cell which highly produces a protein that has previously not been seen can be expected. Since the present invention can be used jointly with a growing method such as fed batch culturing and perfusion culturing as described above, the objective protein producing ability of the recombinant animal cell can be further potentiated. Therefore, the present invention enables considerable cost down due to further production amount potentiation in industrialization of proteins which were difficult to produce in the conventional recombinant animal cells, and were difficult to be industrialized, and also in protein production which has already been industrialized.

The following examples further specifically describe the present invention, but the present invention is not limited to these examples. In the following examples, unless otherwise is indicated, reagents manufactured by Wako Pure Chemical Industries, Takara Shuzo, Toyobo, New England BioLabs, Amersham Pharmacia, BIO-RAD, Sigma, and GIBCO BRL were used.

Example 1

Isolation Of Fibrinogen Gene

For a human fibrinogen gene, Human Liver Marathon-Ready cDNA (BD Bioscience) was used as a template, each two of Kozak sequences and those sequences with a necessary enzyme site added thereto for an α chain, a β chain and a γ chain were prepared as a primer (SEQ ID NOS: 1 to 6), and a PCR reaction was performed using Advantage HF-2 PCR Kit (BD Bioscience) according to a protocol of the kit. As a result, a band of PCR amplification was detected in each of the α chain, the β chain and the γ chain. Since sizes were consistent with the known sizes of α chain, β chain and γ chain, cDNA genes, these genes were cloned (pFbgA, pFbgB and pFbgG, respectively) using a TA cloning kit (Invitrogen), and nucleotide sequences thereof were determined using ABI PRISM310 Genetic Analyzer (PE Biosystems). As a result, FbgA, FbgB and FbgG genes which are shown in SEQ ID NOS: 7 to 9, respectively, were obtained.

Example 2

Construction Of Fibrinogen Gene Expression Vector

Fibrinogen β chain and γ chain gene expression vector pCAGGD-GB, and fibrinogen α chain and γ chain gene expression vector pCAGGDN5-GA used in this example were constructed as follows. For pCAGGD-GB, first, pCAGG-S1 dhfr (WO 03/004641) was digested with BamHI, end-blunted with a T4 DNA polymerase, and ligated using a phosphorylation NotI linker (Takara Shuzo) to construct pCAGG-S1 dhfrN, and a SalI fragment of an FbgG gene derived from pFbgG was incorporated into a SalI site thereof to construct pCAFFD-G. Further, pCAGG (Xho) (WO 03/004641) was digested with SalI, end-blunted with a T4 DNA polymerase, and ligated using the phosphorylation NotI linker (Takara Shuzo) to construct pCAGG (Xho)N, a XbaI- BamHI fragment containing SalI of pCAGG-S1 (WO 03/004641) was incorporated into a XbaI-BamHI site of this plasmid, a BamHI site of the resulting plasmid was digested, end-blunted with a T4 DNA polymerase, and ligated using the phosphorylation NotI linker (Takara Shuzo) to construct pCAGG-S1 2N. A SalI fragment of an FbgB gene derived from pFbgB was incorporated into a SalI site of this pCAGG-S1 2N to construct pCAGG-B. A NotI fragment containing an FbgB gene of pCAGG-B was incorporated into a NotI site of pCAGGD-G to construct final fibrinogen β chain and γ chain expression vector pCAGGD-GB (FIG. 1).

On the other hand, for pCAGGN5-GA, initially, pCAGG-S1 dhfr neo (WO 03/004641) was incompletely digested with BamHI, end-blunted with a T4 DNA polymerase, this was self-ligated as it was to delete a 3' BamHI site of a neo gene among two BamHI sites, this was further digested with BamHI, end-blunted with a T4 DNA polymerase, and ligated using the phosphorylation NotI linker (Takara Shuzo) to construct pCAGG-S1 dhfr neoN (pCAGGDN5-NotI). A SalI fragment containing an FbgG gene derived from pFbgG was inserted into a SalI site of this pCAGG-S1 dhfr neoN to construct a plasmid, and a NotI fragment containing an FbgA gene of pCAGG-A which had been constructed by inserting a SalI fragment containing an FbgA gene derived from pFbgA into a SalI site of pCAGG-S1 2N was incorporated into a NotI site of the plasmid to construct pCAGGDN5-GA (FIG. 1).

Example 3

Preparation of Recombinant Fibrinogen Expressing Cell

Introduction of Cell into Expression Vector, Gene Amplification, Cloning

According to a method which will be described below using the fibrinogen expression plasmids pCAGGD-GB and pCAGGDN5-GA constructed in Example 2, a CHO DG44 (Urlaub G et al., Somatic cell. Mol. Genet., 12, 555 (1986), hereinafter CHO) cell was transformed. On the day before transformation, a CHO cell was seeded on a 6 well plate at a cell density of 1 to $0.5 \times 10^5$ cells/2 ml/well using a YMM medium (nucleic acid-free MEM alpha medium enriched in amino acid-vitamin containing insulin, transferring, ethanolamine and sodium selenite) containing 10% bovine fetal serum (FCS, manufactured by GIBCO-BRL). After cultured at 37° C. overnight in a 5% $CO_2$ culturing apparatus, using a liposome transformation reagent, TransIT-LT1 (Takara Shuzo) or lipofectamine 2000 (Invitrogen), each equal amount of fibrinogen expression plasmids pCAGGD-GB and pCAGGDN5-GA were mixed, and digested and linearized with PvuI in advance and, using this as an introduction DNA, transfection was performed according to each protocol. After cultured at 37° C. overnight in a 5% $CO_2$ culturing apparatus, the medium was exchanged with a selective medium, a YMM medium containing 10% dialysis FCS (d-FCS: manufactured by GIBCO-BRL), 0.5 mg/ml Geneticin (G418: manufactured by GIBCO-BRL), and 100 nM methotrexate (MTX: manufactured by Wako Pure Chemical Industries), or a YMM medium containing 10% d-FCS, and 0.5 mg/ml G418. By continuing culturing at 37° C. in a 5% $CO_2$ culturing apparatus while a medium was exchanged every 3 to 4 days, selection was performed to obtain a transformant.

Fibrinogen production of the resulting transformed cell was measured with ELISA. ELISA was performed by the following procedure. 100 μl of an anti-human fibrinogen-rabbit polyclonal antibody (Dako Cytomation) which had been adjusted to 10 μg/ml with PBS (137 mM NaCl, 8 mM $Na_2HPO_4$-$12H_2O$, 2.7 mM KCl, 1.5 mM $KH_2PO_4$) was applied to an immunomodule plate (Nunc C8-445101), and this was allowed to stand at 4° C. overnight to perform solid phasing. An antibody solution of the solid-phased plate was removed, and this was washed with 390 μl of PBS three times. Subsequently, 370 μL of Block Ace (Dainippon Pharmaceutical) which had been diluted 4-fold with PBS was applied, and blocking was performed at room temperature for 30 minutes to 2 hours. After blocking, a blocking solution was removed, and each 100 μL of a sample (culture supernatant) and a standard were applied. A sample (culture supernatant of fibrinogen producing cell) was diluted 100 to 800-fold using Block Ace which had been diluted 10-fold with PBS. As the standard, Bolheal (manufactured by KAKETSUKEN: vial 1 containing plasma-derived fibrinogen was dissolved according to the specification, and this was diluted to 1 mg/ml with PBS by calculation letting the fibrinogen amount to be 80 mg/ml) was diluted to 100 ng/ml to 1 ng/ml with the same diluent as that of a sample, and this was used. A sample and a standard were reacted at 37° C. for 1 hour after application to a plate. After completion of the reaction, the resultant was washed with 390 μl of a washing solution (0.05% Tween-20/PBS) four times, subsequently, 100 μl of an anti-human fibrinogen-rabbit polyclonal antibody-peroxidase label which had been diluted 8000-fold with a solution (Block Ace which had been diluted 10-fold with PBS)) used in the sample dilution was applied to react at 37° C. for 1 hour. After completion of the reaction, the reaction was washed with 390 μl of a washing solution (0.05% Tween-20/PBS) four times. For color development, 100 μl of TMB Substrate Kit (Kirkegaard & Perry Laboratories) was applied and, after allowing to stand for 30 minutes in the dark place, the reaction was stopped with 100 μl of 1N sulfuric acid. Within 30 minutes after the reaction stoppage, an absorbance at 450 nm to 650 nm was measured with a plate reader (Molecular Device), and a fibrinogen concentration was obtained from a calibration line.

By this ELISA, a transformed cell having the high fibrinogen producing ability was selected and, then, an MTX gene was amplified. A cell was suspended in a YMM medium containing 10% d-FCS and 0.5 mg/ml G418 and having an increasing amount of MTX, this was seeded on a 24 well plate at $5 \times 10^4$ cells/0.5 ml/well, selection was performed by continuing culturing at 37° C. in a 5% $CO_2$ culturing apparatus while a medium was exchanged every 3 to 4 days, to obtain a transformant resistant to MTX at a high concentration. As a result, a cell having a production amount (production amount in a culture supernatant obtained by completely exchanging a medium with a fresh medium when a cell is confluent, and culturing this overnight) of about 20 to 45 μg/ml was obtained. Further, such a recombinant fibrinogen producing cell was cloned. The cell was suspended in a YMM medium containing 10% d-FCS, and each one/200 μl/well was seeded on a 96 well plate, so that cloning was performed. When the medium was completely exchanged with a fresh medium at confluence, and the resulting clone was cultured overnight and a production amount in a culture supernatant was examined, a clone reaching up to 56.8 μg/ml was obtained. Among them, a cell of one clone CH002-24-4 was suspended in a YMM medium containing 10% d-FCS, 0.5 mg/ml G418 and 100 nM MTX, this was seeded on a 6 well plate at $2 \times 10^5$ cells/2 ml/well, cultured for 4 days, an amount of fibrinogen in a culturing supernatant was measured by an ELISA method, it was found that an amount reached 103.3 μg/ml, and it was shown that a production amount of fibrinogen by a recombinant animal cell first exceeded an order of 100 µg/ml.

Example 4

Serum-Free Culturing of Recombinant Fibrinogen Producing Cell

The producing ability of a recombinant fibrinogen producing cell at serum-free culturing was investigated. The clone CH002-24-4 exhibiting a production amount of 100 µg/ml or more in Example 3 was washed with PBS two times, suspended in a medium shown in Table 1 (CHO-S-SFMII, and IS CHO-V is a serum-free medium, and 10% d-FCS/YMM is a serum medium), seeded on a 6 well plate at $10^5$ cells/ml and 2 ml/well, cultured for 4 days, the number of the resulting cells was counted, and a production amount of fibrinogen in a culture supernatant was measured by the aforementioned ELISA. As a result, as shown in Table 1, the fibrinogen producing ability per $1 \times 10^4$ cells was higher as compared with the case where the serum medium (YMM medium containing 10% d-FCS) was used, and it was shown that there is the producing ability equivalent to or superior over that of a serum medium even in a serum-free medium. This shows that since 1 to $2 \times 10^6$ cells/ml can be attained in a general high density culturing, there is the potential ability of producing 440 to 1,520 µg/ml or more of fibrinogen by simple calculation, when the culturing condition is better.

TABLE 1

| Medium | Manufacturer | Production amount (µg/1 × $10^4$ cells) |
|---|---|---|
| 10% d-FCS/YMM | Self preparation | 2.0 |
| CHO-S-SFMII | GIBCO | 4.4 |
| IS CHO-V | IS Japan | 7.6 |

Further, a CH002-24-4 cell grown on this CHO-S-SFMII medium was seeded on 100 ml of an improved serum-free medium based on the same CHO-S-SFMII medium at $1.6 \times 10^5$ cells/ml, and a production amount of 272.7 µm/ml was attained by suspension culturing (rotation number: 45 rpm) for about 2 weeks using a spinner flask manufactured by Techne. Like this, a cell established by the method of the present invention attained a production amount of up to about 270 µg/ml on a serum-free medium regarding fibrinogen production, and it was shown that the cell is a high production cell which has never been seen.

Example 5

Cloning of P35 Gene and Construction of Expression Vector

From a virus solution ($2 \times 10^7$ pf/ml) derived from baculovirus AcNPV (Autographa California nuclear polyhedrosis virus: purchased from Invitrogen), a virus genome was prepared by proteinase K treatment and phenol extraction, this was used as a template, each two of Kozak sequences and those sequences with a necessary enzyme site added thereto for 5' and 3' were prepared as a primer (SEQ ID NOS: 10 and 11), and a PCR reaction was performed using Advantage HF-2 PCR Kit (BD Bioscience). Since a size of the PCR product was consistent with a size of the known P35 gene, this was TA-cloned (Invitrogen). A nucleotide sequence of the resulting plasmid was determined using ABI PRISM310 Genetic Analyzer (PE Biosystems) and, as a result, a pP35 gene clone (SEQ ID NO: 12) having the same sequence as a sequence of the document (Friesen P D, Miller L K., J Virol. 61 (7): 2264-72. 1987) was obtained.

In order to introduce a P35 gene into a cell already expressing fibrinogen, first, as a selectable marker, a vector having a puromycin resistant gene was constructed. In order to insert a BamHI site between SapI and NotI sites of an expression plasmid pCAGG-S1 mdhfr (WO 03/004641) having a mutation DHFR in which $23^{rd}$ serine is arginine, two linkers of GGC CGC GGA TCC GCT CTT CC and AGC CGA AGA GCG GAT CCG C were synthesized, and linker ligation was performed to construct pCAGGM5. Further, pCAGGM5 was digested with BamHI, end-blunted with a T4 DNA polymerase, and linker ligation was performed using a XhoI linker (Takara Shuzo) to introduce XhoI. A SalI fragment containing a puromycin resistant gene of pPGKPuro (Watanabe, S., Kai, N., Yasuda, M., Kohmura, N., Sanbo, M., Mishina, M., and Yagi, T. (1995)) was inserted into a XhoI site of this plasmid to construct pCAGGMP5-NotI. Then, a SalI-NotI fragment containing a mutated DHFR (mdhfr) gene was removed from this plasmid, and instead, a SalI-NotI fragment containing a DHFR gene of pCAGGDN5-NotI was inserted to construct pCAGGDP5-NotI. A XhoI fragment of a PCR-cloned P35 gene was inserted into a SalI site of pCAGGDP5-NotI to construct objective pCAGGDP5-p35 (FIG. 2).

Example 6

P35 Gene Transformed Cell

According to the following method using the P35 expression plasmid pCAGGDP5-p35 constructed in Example 4, a recombinant fibrinogen producing clone, a CH002-24-4 cell was transformed. The CH002-24-4 cell was seeded on a 12 well plate at a cell density of 1 to $0.5 \times 10^5$ cells/ml/well using a CHO-S-SFMII medium (GIBCO-BRL). Using lipofectamine 2000 (Invitrogen) which is a liposome transformation reagent, the P35 expression plasmid pCAGGDP5-p35 was digested and linearized with PvuI in advance and, using this as an introduction DNA, transfection was performed according to a protocol for lipofectamine 2000. After cultured at 37° C. overnight in a 5% $CO_2$ culturing apparatus, the medium was exchanged with a CHO-S-SFMII medium containing 4 µg/ml puromycin (BD Bioscience) as a selected medium. Selection was performed by continuing the culturing at 37° C. in a 5% $CO_2$ culturing apparatus while a medium was exchanged every 3 to 4 days, to obtain a transformant.

Figure 4:
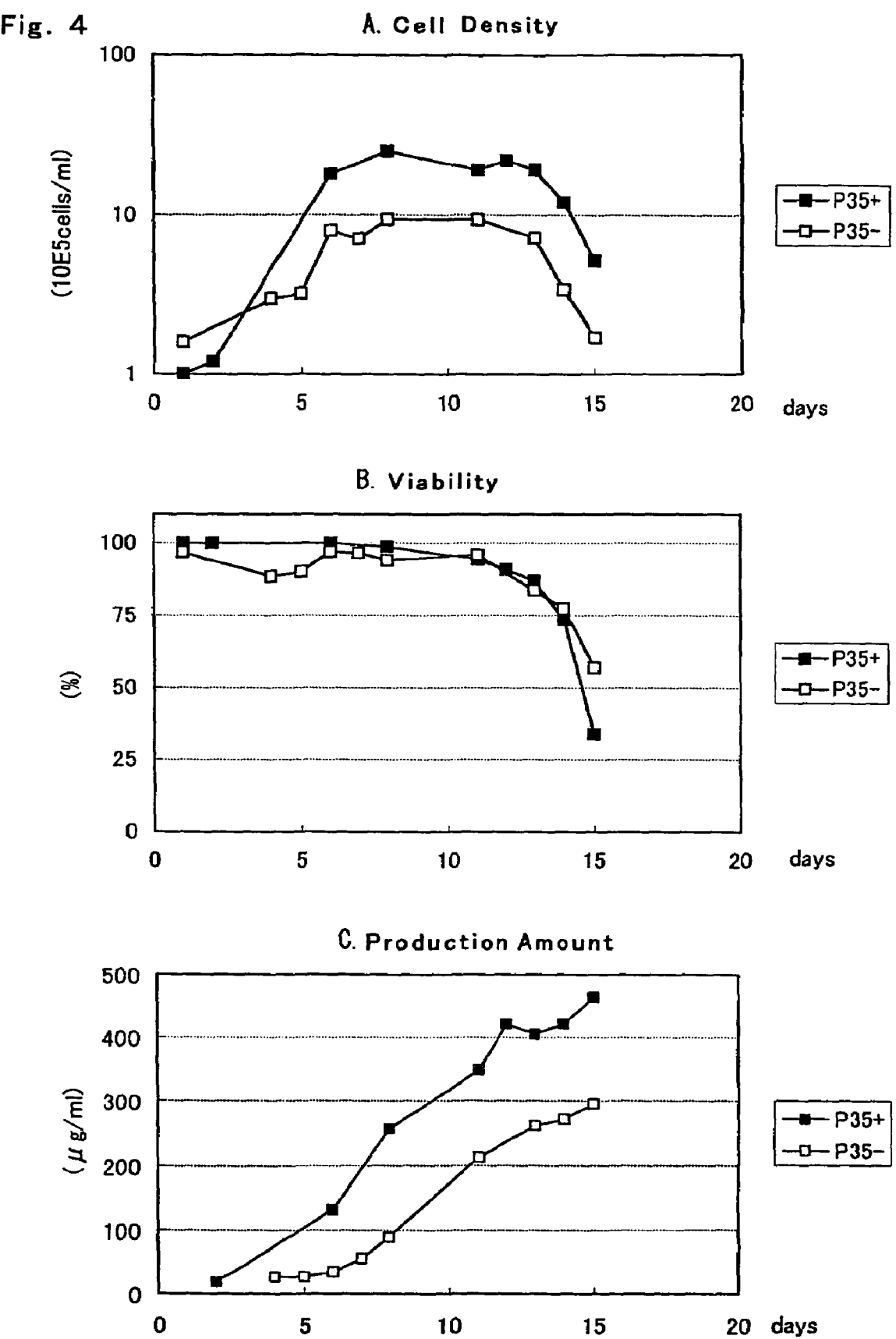
FIG. 4 A-C respectively, show a change with time in a cell density, viability and a fibrinogen production amount in spinner culturing of a cell expressing a baculovirus P35 gene and a cell not expressing the gene.

In order to investigate the effect of an introduced P35 gene, a P9GD cell which is one of the resulting P35 gene transformants and a 2-24-4 cell which is a parent strain thereof were seeded on 100 ml of a CHO-S-SFMII medium at about $1.0 \times 10^5$ cells/ml, suspension culturing (rotation number: 45 rpm) was performed for about 2 weeks using a spinner flask manufactured by Techne, and a proliferation curve, a viability and a fibrinogen production amount were investigated. As a result, as shown in FIG. 3, a maximum cell density of the P9GD cell was $2.2 \times 10^6$ cells/ml, and a maximum cell density of the 2-24-4 cell was $7.2 \times 10^5$ cells/ml, resulting in about 3-fold increase. In addition, the P9GD cell reached 50% viability, being late by 3 days as compared with the 2-24-4 cell. As a result, the production amount on $15^{th}$ day of the culturing was 365.2 µg/ml in the case of the P9GD cell, and 162.7 µg/ml in the case of the 2-24-4 cell, resulting in about 2.2-fold increase. Further, the spinner culturing was performed similarly using an improved serum-free medium enriched in a nutrient component based on the CHO-S-SFMII medium, there was little difference in viability as shown in FIG. 4, but the maximum cell density of the P9GD cell was $2.5 \times 10^6$ cells/ml, while the maximum cell density of the 2-24-4 cell was $9.4 \times 10^5$ cells/ml, resulting in about 2.6-fold increase. Further, the production amount on $15^{th}$ day of the culturing was 463.7 μg/ml in the case of the P9GD cell, while the amount of the 2-24-4 cell was 295.6 μg/ml, resulting in about 1.6-fold increase.

Figure 5:
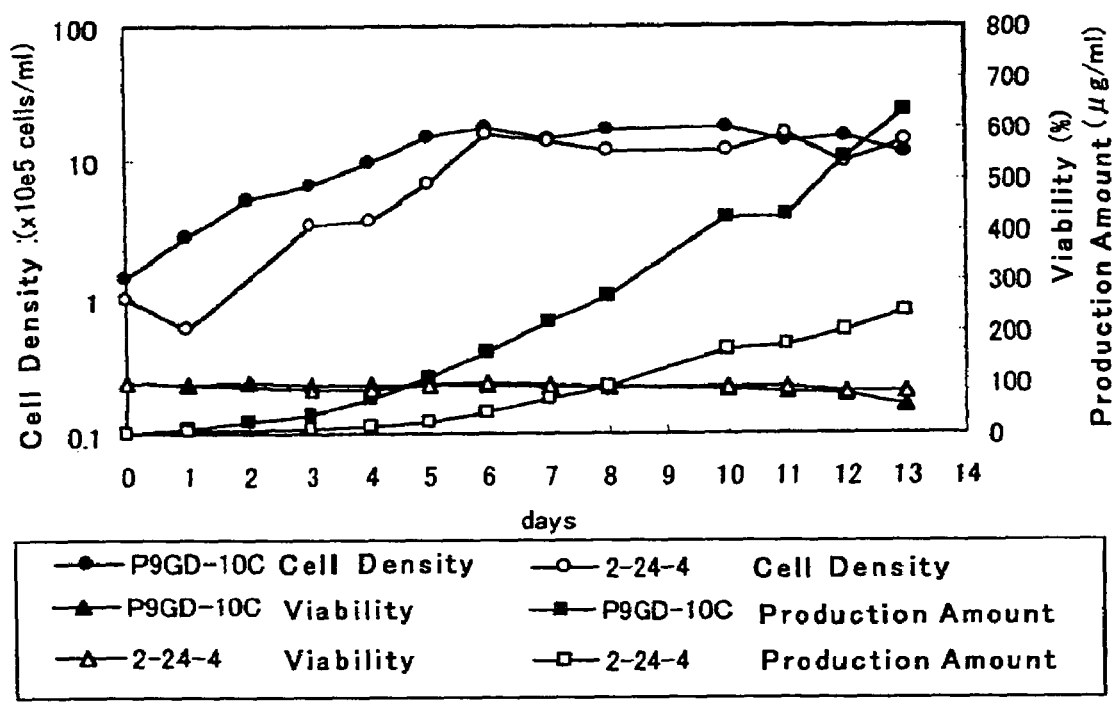
FIG. 5 shows a change with time in a cell density, viability and a fibrinogen production amount in spinner culturing of a cell expressing a baculovirus P35 gene and a cell not expressing the gene.

The P9GD cell was cloned. A cell was suspended in an improved serum-free medium based on a CHO-S-SFMII medium, and 50/200 μl/well of this was seeded on a 96 well plate, so that cloning was performed. Regarding the resulting clone P9GD-10C, the spinner culturing was performed similarly using an improved serum-free medium enriched in a nutrient component based on the CHO-S-SFMII medium as in the P9GD cell, there was no difference in viability and a reaching live cell density, and a production amount on 13 days of the culturing was 631.5 μg/ml, while the amount of the 2-24-4 cell was 239.8 μg/ml, resulting in about 2.6-fold increase (FIG. 5). Since there is no difference in viability and the number of live cells, it was thought that the production amount was increased not by anti-apoptosis action of P35 but by protein biosynthesis potentiating action possessed by P35.

As described in the item of "MEANS FOR SOLVING THE PROBLEMS", the maximum production amount of fibrinogen known before the present invention was about 15 μg/ml, but when a P35 gene was introduced in accordance with the present invention, the amount was 631.5 μg/ml at a spinner culturing level, resulting in about 42-fold production amount potentiating effect. In addition, since the potential fibrinogen producing ability of the 2-24-4 cell which is a parent strain for P35 gene introduction is estimated to be 440 to 1,520 μm/ml or more and, therefore, when a P35 gene is introduced, there is about 1.6 to 2.6-fold effect, it is presumed that a potential production amount of about 704 to 3,952 μg/ml is possessed by simple calculation. Like this, it was shown that a cell established by the method of the present invention is a recombinant animal cell which highly produces a protein which has never been seen.

Example 7

Introduction of P35 Gene into Recombinant Ecarin Producing Cell

Ecarin is a protease derived from snake venom isolated and purified from Echis carinatus (T. Morita et al.,: J. Biochem. 83, 559-570, 1978), and is known to specifically activate prothrombin. A P35 gene was introduced into a SP2/0 mouse myeloma cell expressing a cDNA of this ecarin (Japanese Patent Application No. 2001-206918), and the effect thereof was investigated.

A recombinant ecarin producing SP2/0 cell was washed with cooled Dulbecco's PBS (−) two times, and $10^7$ cells suspended in 0.8 ml of PBS (−) were placed into an Electroporation cuvette (electrode width 0.4 cm, manufactured by BIO-RAD). 40 μg of the aforementioned linearized P35 gene expression plasmid was added, and this was mixed with a pipette. Using Gene Pulser II (manufactured by BIO-RAD), a pulse was applied once at 0.22 kv and 975 μF. The cuvette was cooled on an ice for 10 minutes, the cell suspension was diluted to about 5,000/50 μl with a nucleic acid-containing MEM alpha medium containing 10% bovine fetal serum (FCS), and the dilution was seeded on five 96 well plates at 50 μl/well, and cultured at 35° C. overnight in a 3% $CO_2$ culturing apparatus. On the next day, 50 μl/well of a MEM alpha medium containing 10% FCS was added, followed by further culturing overnight. On the next day, 100 μl/well of a MEM alpha medium containing 8 μg/ml Puromycin and 10% FCS was added. After the culturing for 10 days to 14 days, an appeared transformant was assessed for the producing ability every well. Two well cells having a highest production amount, P35-44 and P35-67 were shake flask cultured (30 ml scale, 1000 rpm) on an MEM alpha medium containing 10% FCS, and a production amount was compared with a cell before P35 gene introduction. Results are shown in FIG. 6. By the culturing for 11 days, there was little difference in cell proliferation and viability as compared with the cell before introduction, or rather there was a tendency in decrease. However, the production amount of the cell before introduction was 5.96 U/ml, while the amount of the P35-44 cell was 12.8 U/ml, and the amount of the P35-67 cell was 18.8 U/ml, exhibiting 2.1 to 3.2-fold potentiating effect. Like this, the baculovirus P35 showed production potentiating action even in the case where apoptosis suppressing effect was not exhibited.

Example 8

Introduction of P35 Gene into Recombinant Factor VIII Producing Cell

Factor VIII is involved in blood coagulation intrinsic system, and is an important coagulation factor for maintaining normal hemostatic mechanism, and congenital activity deficiency induces coagulation disorder of sex-linked recessive inheritance called hemophilia A. A P35 gene was introduced into a BHK21 cell expressing this factor VIII cDNA gene, and the effect of the P35 gene was investigated.

For a factor VIII gene, a PCR reaction was performed using Advantage-GC2 Polymerase Mix (BD Bioscience) employing Human Liver cDNA (BD Bioscience) as a template and SEQ ID NOS: 14 and 15 as a primer according to a nucleic acid nucleotide sequence of the literature of J. Gitschier et al. (Nature, 312, 326, 1984). After a nucleic acid nucleotide sequence of the PCR product was determined as described in the literature, the product was finally cut with XhoI and SalI, and inserted into a SalI site of pCAGG-S1 dhfr neo (WO 03/004641) to construct a factor VIII expression vector. The BHK21 cell was transfected with a factor VIII gene expression plasmid according to the same method as that of Example 7, and a transformed cell was prepared. As a medium, an EX-CELL325 medium (JRH) containing 10% transparent FBS was used, and selection was performed by double selection (G418, MTX 0.5 ∞M, MTX 0.75 μM). Further, gene amplification with MTX was performed using the resulting production strain. Using EX-CELL325 as a medium, a MTX concentration was increased at a step manner starting at a MTX concentration of 0.5 μM and, finally, a factor VIII producing cell having a production amount increased to about 5-fold at the MTX concentration of 10 μM was obtained. These cells were cloned by a limiting dilution method, to obtain a KMT strain stably producing the factor VIII which was used in this example.

A P35 gene expression plasmid was introduced into this KMT cell by the method shown in Example 6. Then, pCAG-GDP5-p35 was cut with PvuI, and introduced using Lipofectamine 2000 (Invitrogen). Using EX-CELL325 containing Puromycin as a selective medium, selection was performed on a 12 well plate. The resulting transformed cell was seeded (1×10e5/ml/well of 24 plate) by adjusting the number of cells and, on day 3, a culture supernatant was recovered, and the production amount potentiating effect was studied by comparing with a parent strain. As a result, in all of cells with the P35 gene introduced therein, an expression amount was increased higher than the KMT cell which is a parent strain and, particularly, in cells shown in the following table, a 2.4 to 4.4-fold increase was obtained. Since all of these cells had viability of 90% or more, it was thought that the production amount was increased not by anti-apoptosis action of P35 but by protein biosynthesis potentiating action possessed by P35.

TABLE 2

| Cell | Viability % | Production amount mU/10e5 | Fold |
|---|---|---|---|
| KMT | 92.4 | 21.8 | 1.0 |
| KMTP-1 | 90.2 | 95.0 | 4.4 |
| KMTP-2 | 94.1 | 64.1 | 2.9 |
| KMTP-7 | 90.8 | 66.4 | 3.0 |
| KMTP-9 | 96.5 | 55.2 | 2.5 |
| KMTP-10 | 97.2 | 52.2 | 2.4 |

INDUSTRIAL APPLICABILITY

Since it becomes possible to highly produce an objective protein when the present invention is used, the present invention has a high utilization value in the medicament industry requiring mass-production of a protein by the recombination technique and other industries requiring a protein at a large amount in a bioreactor and a detergent. Inter alia, the present invention is particularly useful in medicaments or reagents for research because there are many kinds of proteins which cannot be produced not by an animal cell. Further, since the present invention exerts the effect even under the condition for culturing an animal cell which has previously been performed, it becomes possible to highly produce a protein utilizing the existing facilities. In addition, since a cell transformed with a gene encoding a factor having caspase activity inhibiting action and/or protein biosynthesis activity potentiating action before introduction of a protein gene obtained by the present invention becomes possible to produce an objective protein at a large amount only by introducing a gene of a protein to be produced, it becomes possible to utilize in production of a wide range of objective proteins in the wide field.

In particular, since a recombinant ecarin producing cell, a recombinant factor VIII producing cell, and a recombinant fibrinogen producing cell obtained by the present invention highly produce ecarin, factor VIII and fibrinogen, safety is considerably improved, and supply becomes stable as compared with the previous preparations derived from blood of an animal or human. These proteins enable to provide medicaments such as agents for arresting, preventing or treating ingravescence of morbid state for various diseases by using alone or in combination with other proteins or various additives such as a stabilizer, a protective agent and an antiseptic. For example, the fibrinogen obtained by the present invention is used in improvement in the consumption state of a blood coagulation factor such as DIC, or in replenishing therapy in congenital and acquired fibrinogen deficiency. In addition, the thrombin prepared by the human fibrinogen and the ecarin obtained by the present invention is utilized as a tissue adhesive utilizing adherence of fibrin, in a wide range of therapy such as hemostasis, enclosure of a wound site, adhesion or suture-reinforcing of nerve, tendon, vessel and tissue, and closure of air leakage in lung, or as a suitable drug for a base of regeneration therapy for the purpose of regenerating a tissue. In addition, these proteins are useful in progression of research associated with blood coagulation and fibrinogenolysis as an antigen upon preparation of monoclonal-polyclonal antibodies, or as a reagent itself, in addition to as medicaments.

Like this, a recombinant protein highly producing cell obtained by the method of the present invention, and a protein obtained by the recombinant animal cell greatly contribute in the fields of medicine and research.

The invention claimed is:

1. A recombinant mammalian animal cell transformed with a baculovirus p35 gene encoding a protein that inhibits caspase activity and/or potentiates protein biosynthesis, and a gene encoding for a protein selected from the group consisting of ecarin, fibrinogen, and blood coagulation factor VIII.

2. The recombinant animal cell according to claim 1, wherein the animal cell is selected from the group consisting of a Chinese hamster ovary cell (CHO cell), a mouse myeloma cell, a BHK cell, a 293 cell, and a COS cell.

3. The recombinant animal cell according to claim 2, wherein the animal cell is any one of a Chinese hamster ovary cell (CHO cell) DG44 strain, a BHK21 strain, and a mouse myeloma SP2/0 strain.

4. The recombinant animal cell according to claim 1, comprising an expression vector for expressing the baculovirus p35 gene and the gene encoding the protein selected from the group consisting of ecarin, fibrinogen, and blood coagulation factor VIII, wherein the expression vector contains a promoter selected from the group consisting of a SV40 early promoter, a SV40 late promoter, a cytomegalovirus promoter and a chicken β-actin promoter, as well as a marker gene selected from the group consisting of an aminoglycoside 3' phosphotransferase (neo) gene, a puromycin resistant gene, a dihydrofolate reductase (dhfr) gene, and a glutamine synthesis enzyme (GS) gene.

5. The recombinant animal cell according to claim 1, wherein comprising an expression vector having a chicken β-actin promoter and the baculovirus P35 gene.

6. The recombinant animal cell according to claim 1, comprising an expression vector having a cytomegalovirus enhancer and the baculovirus P35 gene.

7. The recombinant animal cell according to claim 1, wherein the protein to be produced is a secretion protein.

8. The recombinant animal cell according to claim 7, wherein the protein to be produced is ecarin.

9. The recombinant animal cell according to claim 1, wherein the protein to be produced is a protein present in blood.

10. The recombinant animal cell according to claim 7, wherein the protein to be produced is fibrinogen.

11. The recombinant animal cell according to claim 7, wherein the protein to be produced is blood coagulation factor VIII.

12. A method for mass-producing a protein, said method comprising culturing the recombinant animal cell according to claim 1 under a culture condition so that apoptosis is not induced.

13. The method according to claim 12, wherein the culturing method is any one of a fed batch culturing method, a perfusion culturing method, and a culturing method using a nutrient-enriched medium.

14. The method according to claim 12, wherein a serum-free medium is used.

15. The method according to claim 12, wherein the protein has a production amount, which can be increased up to about 4,000 μg/ml.

16. A method for preparing the recombinant animal cell according to claim 1, wherein the animal cell is transformed in such a manner that the baculovirus p35 gene and the gene encoding for a protein selected from the group consisting of ecarin, fibrinogen, and blood coagulation factor VIII are introduced into the animal cell simultaneously or at different times.

* * * * *

SEQUENCE LISTING

<160> NUMBER OF SEQ ID NOS: 16

<210> SEQ ID NO 1
<211> LENGTH: 45
<212> TYPE: DNA
<213> ORGANISM: Human

<400> SEQUENCE: 1
ccccaagctt gtcgacgcca ccatgttttc catgaggatc gtctg          45

<210> SEQ ID NO 2
<211> LENGTH: 60
<212> TYPE: DNA
<213> ORGANISM: Human

<400> SEQUENCE: 2
ccatcgatgg atccgtcgac ttactagggg gacagggaag gcttccccaa aggagaagtg      60

<210> SEQ ID NO 3
<211> LENGTH: 60
<212> TYPE: DNA
<213> ORGANISM: Human

<400> SEQUENCE: 3
ccccaagctt gtcgacgcca ccatgaaaca tctattattg ctactattgt gtgttttct       60

<210> SEQ ID NO 4
<211> LENGTH: 60
<212> TYPE: DNA
<213> ORGANISM: Human

<400> SEQUENCE: 4

```
cggaattctg atcagtcgac ttactattgc tgtgggaaga agggcctgat cttcatactc    60
```

<210> SEQ ID NO 5
<211> LENGTH: 56
<212> TYPE: DNA
<213> ORGANISM: Human

<400> SEQUENCE: 5

```
ccccaagctt gtcgacgcca ccatgagttg gtccttgcac ccccggaatt taattc        56
```

<210> SEQ ID NO 6
<211> LENGTH: 51
<212> TYPE: DNA
<213> ORGANISM: Human

<400> SEQUENCE: 6

```
cggaattcgg atccgtcgac ttattaaacg tctccagcct gtttggctcc c             51
```

<210> SEQ ID NO 7
<211> LENGTH: 1980
<212> TYPE: DNA
<213> ORGANISM: Human

<400> SEQUENCE: 7

```
ccccaagctt gtcgacgcca ccatgttttc catgaggatc gtctgcctgg tcctaagtgt    60
ggtgggcaca gcatggactg cagatagtgg tgaaggtgac tttctagctg aaggaggagg   120
cgtgcgtggc ccaaggggttg tggaaagaca tcaatctgcc tgcaaagatt cagactggcc   180
cttctgctct gatgaagact ggaactacaa atgcccttct ggctgcagga tgaaagggtt   240
gattgatgaa gtcaatcaag attttacaaa cagaataaat aagctcaaaa attcactatt   300
tgaatatcag aagaacaata aggattctca ttcgttgacc actaatataa tggaaatttt   360
gagaggcgat ttttcctcag ccaataaccg tgataatacc tacaaccgag tgtcagagga   420
tctgagaagc agaattgaag tcctgaagcg caaagtcata gaaaaagtac agcatatcca   480
gcttctgcag aaaaatgtta gagctcagtt ggttgatatg aaacgactgg aggtggacat   540
tgatattaag atccgatctt gtcgagggtc atgcagtagg gctttagctc gtgaagtaga   600
tctgaaggac tatgaagatc agcagaagca acttgaacag gtcattgcca agacttact   660
tccctctaga gataggcaac acttaccact gataaaaatg aaaccagttc cagacttggt   720
tcccggaaat tttaagagcc agcttcagaa ggtaccccca gagtggaagg cattaacaga   780
catgccgcag atgagaatgg agttagagag acctggtgga aatgagatta ctcgaggagg   840
ctccaccctct tatggaaccg gatcagagac ggaaagcccc aggaacccta gcagtgctgg   900
aagctggaac tctgggagct ctggacctgg aagtactgga aaccgaaacc ctgggagctc   960
tgggactgga gggactgcaa cctggaaacc tgggagctct ggacctggaa gtactggaag  1020
ctggaactct gggagctctg gaactggaag tactggaaac caaaaccctg ggagccctag  1080
acctggtagt accggaacct ggaatcctgg cagctctgaa cgcggaagtg ctgggcactg  1140
gacctctgag agctctgtat ctggtagtac tggacaatgg cactctgaat ctggaagttt  1200
```

```
taggccagat agcccaggct ctgggaacgc gaggcctaac aacccagact ggggcacatt   1260
tgaagaggtg tcaggaaatg taagtccagg gacaaggaga gagtaccaca cagaaaaact   1320
ggtcacttct aaaggagata aagagctcag gactggtaaa gagaaggtca cctctggtag   1380
cacaaccacc acgcgtcgtt catgctctaa aaccgttact aagactgtta ttggtcctga   1440
tggtcacaaa gaagttacca agaagtggt gacctccgaa gatggttctg actgtcccga    1500
ggcaatggat ttaggcacat tgtctggcat aggtactctg gatgggttcc gccataggca   1560
ccctgatgaa gctgccttct tcgacactgc ctcaactgga aaaacattcc caggtttctt   1620
ctcacctatg ttaggagagt ttgtcagtga gactgagtct aggggctcag aatctggcat   1680
cttcacaaat acaaaggaat ccagttctca tcaccctggg atagctgaat tcccttcccg   1740
tggtaaatct tcaagttaca gcaaacaatt tactagtagc acgagttaca acagaggaga   1800
ctccacattt gaaagcaaga gctataaaat ggcagatgag gccggaagtg aagccgatca   1860
tgaaggaaca catagcacca agagaggcca tgctaaatct cgccctgtca gaggtatcca   1920
cacttctcct ttggggaagc cttccctgtc cccctagtaa gtcgacggat ccatcgatgg   1980

<210> SEQ ID NO 8
<211> LENGTH: 1479
<212> TYPE: DNA
<213> ORGANISM: Human

<400> SEQUENCE: 8
ccccaagctt gtcgacgcca ccatgaaaca tctattattg ctactattgt gtgtttttct     60
agttaagtcc caaggtgtca cgacaatga ggagggtttc ttcagtgccc gtggtcatcg     120
accccttgac aagaagagag aagaggctcc cagcctgagg cctgccccac cgcccatcag    180
tggaggtggc tatcgggctc gtccagccaa agcagctgcc actcaaaaga agtagaaag    240 aaaagcccct gatgctggag gctgtcttca cgctgaccca gacctggggg tgttgtgtcc    300
tacaggatgt cagttgcaag aggctttgct acaacaggaa aggccaatca gaaatagtgt    360
tgatgagtta ataacaatg tggaagctgt ttcccagacc tcctcttctt cctttcagta    420
catgtatttg ctgaaagacc tgtggcaaaa gaggcagaag caagtaaaag ataatgaaaa    480
tgtagtcaat gagtactcct cagaactgga aaagcaccaa ttatatatag atgagactgt    540
gaatagcaat atcccaacta accttcgtgt gcttcgttca atcctggaaa acctgagaag    600
caaaatacaa aagttagaat ctgatgtctc agctcaaatg gaatattgtc gcaccccatg    660
cactgtcagt tgcaatattc ctgtggtgtc tggcaaagaa tgtgaggaaa ttatcaggaa    720
aggaggtgaa acatctgaaa tgtatctcat tcaacctgac agttctgtca accgtatag    780 agtatactgt gacatgaata cagaaaatgg aggatggaca gtgattcaga accgtcaaga    840
cggtagtgtt gactttggca ggaaatggga tccatataaa cagggatttg gaaatgttgc    900
aaccaacaca gatgggaaga attactgtgg cctaccaggt gaatattggc ttggaaatga    960
taaaattagc cagcttacca ggatgggacc cacagaactt ttgatagaaa tggaggactg   1020
gaaaggagac aaagtaaagg ctcactatgg aggattcact gtacagaatg aagccaacaa   1080
ataccagatc tcagtgaaca atacagagg aacagccggt aatgccctca tggatggagc   1140
atctcagctg atgggagaaa acaggaccat gaccattcac aacggcatgt tcttcagcac   1200
gtatgacaga gacaatgacg gctggttaac atcagatccc agaaaacagt gttctaaaga   1260
agacggtggt ggatggtggt ataatagatg tcatgcagcc aatccaaacg gcagatacta   1320 ctgggggtgga cagtacacct gggacatggc aaagcatggc acagatgatg gtgtagtatg   1380
```

```
gatgaattgg aagggggtcat ggtactcaat gaggaagatg agtatgaaga tcaggccctt    1440
cttcccacag caatagtaag tcgactgatc agaattccg                            1479

<210> SEQ ID NO 9
<211> LENGTH: 1359
<212> TYPE: DNA
<213> ORGANISM: Human

<400> SEQUENCE: 9
ccccaagctt gtcgacgcca ccatgagttg gtccttgcac ccccggaatt taattctcta      60
cttctatgct cttttatttc tctcttcaac atgtgtagca tatgttgcta ccagagacaa     120
ctgctgcatc ttagatgaaa gattcggtag ttattgtcca actacctgtg gcattgcaga     180
tttcctgtct acttatcaaa ccaaagtaga caaggatcta cagtctttgg aagacatctt     240
acatcaagtt gaaaacaaaa catcagaagt caaacagctg ataaaagcaa tccaactcac     300
ttataatcct gatgaatcat caaaaccaaa tatgatagac gctgctactt tgaagtccag     360
gaaaatgtta aagaaaatta tgaaatatga agcatcgatt ttaacacatg actcaagtat     420
tcgatatttg caggaaatat ataattcaaa taatcaaaag attgttaacc tgaaagagaa     480
ggtagcccag cttgaagcac agtgccagga accttgcaaa gacacggtgc aaatccatga     540
tatcactggg aaagattgtc aagacattgc caataaggga gctaaacaga gcgggcttta     600
ctttattaaa cctctgaaag ctaaccagca attcttagtc tactgtgaaa tcgatgggtc     660
tggaaatgga tggactgtgt ttcagaagag acttgatggc agtgtagatt tcaagaaaaa     720
ctggattcaa tataaagaag gatttggaca tctgtctcct actggcacaa cagaattttg     780
gctgggaaat gagaagattc atttgataag cacacagtct gccatcccat atgcattaag     840
agtggaactg gaagactgga atggcagaac cagtactgca gactatgcca tgttcaaggt     900
gggacctgaa gctgacaagt accgcctaac atatgcctac ttcgctggtg gggatgctgg     960
agatgccttt gatggctttg attttggcga tgatcctagt gacaagtttt tcacatccca    1020
taatggcatg cagttcagta cctgggacaa tgacaatgat aagtttgaag caactgtgc     1080 tgaacaggat ggatctggtt ggtggatgaa caagtgtcac gctggccatc tcaatggagt    1140
ttattaccaa ggtggcactt actcaaaagc atctactcct aatggttatg ataatggcat    1200
tatttgggcc acttggaaaa cccggtggta ttccatgaag aaaaccacta tgaagataat    1260
cccattcaac agactcacaa ttggagaagg acagcaacac cacctggggg agccaaaaca    1320
ggctggagac gtttaataag tcgacggatc cgaattccg                          1359

<210> SEQ ID NO 10
<211> LENGTH: 60
<212> TYPE: DNA
<213> ORGANISM: Baculovirus

<400> SEQUENCE: 10
ccgctcgagg aattcgccac catgtgtgta attttttccgg tagaaatcga cgtgtcccag       60

<210> SEQ ID NO 11
<211> LENGTH: 54
<212> TYPE: DNA
<213> ORGANISM: Baculovirus

<400> SEQUENCE: 11
ccgctcgagg aattctactc gtaaagccag ttcaatttta aaaacaaatg acat            54
```

<210> SEQ ID NO 12
<211> LENGTH: 1035
<212> TYPE: DNA
<213> ORGANISM: Baculovirus

<400> SEQUENCE: 12

| | | | | | |
|---|---|---|---|---|---|
| ccgctcgagg | aattcgccac | catgtgtgta | attttttccgg | tagaaatcga | cgtgtcccag | 60 |
| acgattattc | gagattgtca | ggtggacaaa | caaaccagag | agttggtgta | cattaacaag | 120 |
| attatgaaca | cgcaattgac | aaaacccgtt | ctcatgatgt | ttaacatttc | gggtcctata | 180 |
| cgaagcgtta | cgcgcaagaa | caacaatttg | cgcgacagaa | taaaatcaaa | agtcgatgaa | 240 |
| caatttgatc | aactagaacg | cgattacagc | gatcaaatgg | atggattcca | cgatagcatc | 300 |
| aagtatttta | aagatgaaca | ctattcggta | agttgccaaa | atggcagcgt | gttgaaaagc | 360 |
| aagtttgcta | aaattttaaa | gagtcatgat | tataccgata | aaaagtctat | tgaagcttac | 420 |
| gagaaatact | gtttgcccaa | attggtcgac | gaacgcaacg | actactacgt | ggcggtatgc | 480 |
| gtgttgaagc | cgggatttga | aacggcagc | aaccaagtgc | tatctttcga | gtacaacccg | 540 |
| attggtaaca | aagttattgt | gccgtttgct | cacgaaatta | cgacacggg | actttacgag | 600 |
| tacgacgtcg | tagcttacgt | ggacagtgtg | cagtttgatg | gcgaacaatt | tgaagagttt | 660 |
| gtgcagagtt | taatattgcc | gtcgtcgttc | aaaaattcgg | aaaaggtttt | atattacaac | 720 |
| gaagcgtcga | aaaacaaaag | catgatctac | aaggctttag | agtttactac | agaatcgagc | 780 |
| tggggcaaat | ccgaaaagta | taattggaaa | attttttgta | acggttttat | ttatgataaa | 840 |
| aaatcaaaag | tgttgtatgt | taaattgcac | aatgtaacta | gtgcactcaa | caaaaatgta | 900 |
| atattaaaca | caattaaata | aatgttaaaa | tttattgcct | aatattattt | tgtcattgct | 960 |
| tgtcatttat | taatttggat | gatgtcattt | gttttttaaaa | ttgaactggc | tttacgagta | 1020 |
| gaattcctcg | agcgg | | | | | 1035 |

<210> SEQ ID NO 13
<211> LENGTH: 1863
<212> TYPE: DNA
<213> ORGANISM: Echis carinatus

<400> SEQUENCE: 13

| | | | | | |
|---|---|---|---|---|---|
| ctcgagatga | tccagattct | cttggtaatt | atatgcttag | cagttttttcc | atatcaaggt | 60 |
| tgctctataa | tcctgggatc | tgggaatgtt | aatgattatg | aagtagtgta | tccacaaaaa | 120 |
| gtcactgcat | tgcccaaagg | agcagttcag | cagcctgagc | aaaagtatga | agatgccatg | 180 |
| caatatgaat | ttgaagtgaa | gggagagcca | gtggtccttc | acctagaaaa | aaataaagaa | 240 |
| cttttttcag | aagattacag | tgagactcat | tattcgtctg | atgacagaga | aattacaaca | 300 |
| aacccttcag | ttgaggatca | ctgctattat | catggacgga | tccagaatga | tgctgagtca | 360 |
| actgcaagca | tcagtgcatg | caatggtttg | aaaggacatt | tcaagcttcg | aggggagacg | 420 |
| tactttattg | aacccttgaa | gattcccgac | agtgaagccc | atgcagtcta | caaatatgaa | 480 |
| aacatagaaa | atgaggatga | agcccccaaa | atgtgtgggg | taacccagga | taattgggaa | 540 |
| tcagatgaac | ccatcaaaaa | gactttgggg | ttaattgttc | ctcctcatga | acgaaaattt | 600 |
| gagaaaaaat | tcattgagct | tgtcgtagtt | gtggaccaca | gtatggtcac | aaaatacaac | 660 |
| aatgattcaa | ctgctataag | aacatggata | tatgaaatgc | tcaacactgt | aaatgagata | 720 |
| tacttacctt | tcaatattcg | tgtagcactg | gttggcctag | aatttgtgtg | caatggagac | 780 |
| ttgattaacg | tgacatccac | agcagatgat | actttgcact | catttggaga | atggagagca | 840 |

```
tcagatttgc tgaatcgaaa aagacatgat catgctcagt tactcacgaa cgtgacactg    900
gatcattcca ctcttggaat cacgttcgta tatggcatgt gcaaatcaga tcgttctgta    960
gaacttattc tggattacag caacataact tttaatatgg catatataat agcccatgag   1020
atgggtcata gtctgggcat gttacatgac acaaaattct gtacttgtgg ggctaaacca   1080
tgcattatgt ttggcaaaga aagcattcca ccgcccaaag aattcagcag ttgtagttat   1140
gaccagtata acaagtatct tcttaaatat aacccaaaat gcattcttga tccacctttg   1200
agaaaagata ttgcttcacc tgcagtttgt ggaaatgaaa tttgggagga aggagaagaa   1260
tgtgattgtg gttctcctgc agattgtcga atccatgct gtgatgctgc aacatgtaaa    1320
ctgaaaccag gggcagaatg tggaaatgga gagtgttgtg acaagtgcaa gattaggaaa   1380
gcaggaacag aatgccggcc agcaagggat gactgtgatg tcgctgaaca ctgcactggc   1440
caatctgctg agtgtcccag aaatgagttc caaaggaatg gacaaccatg ccttaacaac   1500
tcgggttatt gctacaatgg ggattgcccc atcatgttaa accaatgtat tgctctcttt   1560
agtccaagtg caactgtggc tcaagattca tgttttcaga ggaacttgca aggcagttac   1620
tatggctact gcacaaagga aattggttac tatggtaaaa ggtttccatg tgcaccacaa   1680
gatgtaaaat gtggcagatt atactgctta gataattcat tcaaaaaaaa tatgcgttgc   1740
aagaacgact attcatacgc ggatgaaaat aagggaatag ttgaacctgg aacaaaatgt   1800
gaagatggaa aggtctgcat caacaggaag tgtgttgatg tgaatacagc ctactaactc   1860
gag                                                                 1863

<210> SEQ ID NO 14
<211> LENGTH: 36
<212> TYPE: DNA
<213> ORGANISM: Human

<400> SEQUENCE: 14
atcactcgag gccaccatgc aaatagagct ctccac                               36

<210> SEQ ID NO 15
<211> LENGTH: 39
<212> TYPE: DNA
<213> ORGANISM: Human

<400> SEQUENCE: 15
ggaggtcgac tcagtagagg tcctgtgcct cgcagccca                             39

<210> SEQ ID NO 16
<211> LENGTH: 7082
<212> TYPE: DNA
<213> ORGANISM: Human

<400> SEQUENCE: 16
atcactcgag gccaccatgc aaatagagct ctccacctgc ttctttctgt gccttttgcg     60
attctgcttt agtgccacca gaagatacta cctgggtgca gtggaactgt catgggacta    120
tatgcaaagt gatctcggtg agctgcctgt ggacgcaaga tttcctccta gagtgccaaa    180
atcttttcca ttcaacacct cagtcgtgta caaaaagact ctgtttgtag aattcacgga    240
tcaccttttc aacatcgcta agccaaggcc accctggatg ggtctgctag gtcctaccat    300
ccaggctgag gttatgata cagtggtcat tacacttaag aacatggctt cccatcctgt    360
cagtcttcat gctgttggtg tatcctactg gaaagcttct gagggagctg aatatgatga    420
```

```
tcagaccagt caaagggaga aagaagatga taaagtcttc cctggtggaa gccatacata    480
tgtctggcag gtcctgaaag agaatggtcc aatggcctct gacccactgt gccttaccta    540
ctcatatctt tctcatgtgg acctggtaaa agacttgaat tcaggcctca ttggagccct    600
actagtatgt agagaaggga gtctggccaa ggaaaagaca cagaccttgc acaaatttat    660 actactttt gctgtatttg atgaagggaa aagttggcac tcagaaacaa agaactcctt     720
gatgcaggat agggatgctg catctgctcg ggcctggcct aaaatgcaca cagtcaatgg    780
ttatgtaaac aggtctctgc caggtctgat tggatgccac aggaaatcag tctattggca    840
tgtgattgga atgggcacca ctcctgaagt gcactcaata ttcctcgaag gtcacacatt    900
tcttgtgagg aaccatcgcc aggcgtcctt ggaaatctcg ccataacctt tccttactgc    960
tcaaacactc ttgatggacc ttggacagtt tctactgttt tgtcatatct cttcccacca   1020
acatgatggc atggaagctt atgtcaaagt agacagctgt ccagaggaac cccaactacg   1080
aatgaaaaat aatgaagaag cggaagacta tgatgatgat cttactgatt ctgaaatgga   1140
tgtggtcagg tttgatgatg acaactctcc ttcctttatc caaattcgct cagttgccaa   1200
gaagcatcct aaaacttggg tacattacat tgctgctgaa gaggaggact gggactatgc   1260
tcccttagtc ctcgcccccg atgacagaag ttataaaagt caatatttga acaatggccc   1320
tcagcggatt ggtaggaagt acaaaaaagt ccgatttatg gcatacacag atgaaacctt   1380
taagactcgt gaagctattc agcatgaatc aggaatcttg ggacctttac tttatgggga   1440
agttggagac acactgttga ttatatttaa gaatcaagca agcagaccat ataacatcta   1500
ccctcacgga atcactgatg tccgtccttt gtattcaagg agattaccaa aaggtgtaaa   1560
acatttgaag gattttccaa ttctgccagg agaaatattc aaatataaat ggacagtgac   1620
tgtagaagat gggccaacta aatcagatcc tcggtgcctg acccgctatt actctagttt   1680
cgttaatatg gagagagatc tagcttcagg actcattggc cctctcctca tctgctacaa   1740
agaatctgta gatcaaagag gaaaccagat aatgtcagac aagaggaatg tcatcctgtt   1800 ttctgtatt tgatgagaacc gaagctggta cctcacagag aatatacaac gctttctccc    1860
caatccagct ggagtgcagc ttgaggatcc agagttccaa gcctccaaca tcatgcacag   1920
catcaatggc tatgtttttg atagtttgca gttgtcagtt tgtttgcatg aggtggcata   1980
ctggtacatt ctaagcattg gagcacagac tgacttcctt tctgtcttct tctctggata   2040
taccttcaaa cacaaaatgg tctatgaaga cacactcacc ctattcccat tctcaggaga   2100
aactgtcttc atgtcgatgg aaaacccagg tctatggatt ctggggtgcc acaactcaga   2160
ctttcggaac agaggcatga ccgccttact gaaggtttct agttgtgaca gaacactgg    2220 tgattattac gaggacagtt atgaagatat ttcagcatac ttgctgagta aaacaatgc    2280 cattgaacca agaagcttct cccagaattc aagcaccct agcactaggc aaaagcaatt   2340
taatgccacc acaattccag aaaatgacat agagaagact gacccttggt ttgcacacag   2400
aacacctatg cctaaaatac aaaatgtctc ctctagtgat tgttgatgc tcttgcgaca    2460 gagtcctact ccacatgggc tatccttatc tgatctccaa gaagccaaat atgagacttt   2520
ttctgatgat ccatcacctg gagcaataga cagtaataac agcctgtctg aaatgacaca   2580
cttcaggcca cagctccatc acagtgggga catggtattt acccctgagt caggcctcca   2640
attaagatta aatgagaaac tggggacaac tgcagcaaca gagttgaaga aacttgattt   2700
caaagtttct agtacatcaa ataatctgat ttcaacaatt ccatcagaca atttggcagc   2760
aggtactgat aatacaagtt ccttaggacc cccaagtatg ccagttcatt atgatagtca   2820
```

```
attagatacc actctatttg gcaaaaagtc atctccccatt actgagtctg gtggacctct    2880
gagcttgagt gaagaaaata atgattcaaa gttgttagaa tcaggtttaa tgaatagcca    2940
agaaagttca tggggaaaaa atgtatcgtc aacagagagt ggtaggttat ttaaagggaa    3000
aagagctcat ggacctgctt tgttgactaa agataatgcc ttattcaaag ttagcatctc    3060
tttgttaaag acaaacaaaa cttccaataa ttcagcaact aatagaaaga ctcacattga    3120
tggcccatca ttattaattg agaatagtcc atcagtctgg caaaatatat tagaaagtga    3180
cactgagttt aaaaaagtga caccctttgat tcatgacaga atgctatgg acaaaaatgc      3240 tacagctttg aggctaaatc atatgtcaaa taaaactact tcatcaaaaa acatggaaat    3300
ggtccaacag aaaaaagagg gccccattcc accagatgca caaatccag atatgtcgtt      3360 ctttaagatg ctattcttgc cagaatcagc aaggtggata caaaggactc atggaaagaa    3420
ctctctgaac tctgggcaag gccccagtcc aaagcaatta gtatccttag gaccagaaaa    3480
atctgtggaa ggtcagaatt tcttgtctga gaaaaacaaa gtggtagtag gaaagggtga    3540
atttacaaag gacgtaggac tcaaagagat ggttttttcca agcagcagaa acctatttct    3600
tactaacttg gataatttac atgaaaataa tacacacaat caagaaaaaa aaattcagga    3660
agaaatagaa aagaaggaaa cattaatcca agagaatgta gttttgcctc agatacatac    3720
agtgactggc actaagaatt tcatgaagaa ccttttctta ctgagcacta ggcaaaatgt    3780
agaaggttca tatgacgggg catatgctcc agtacttcaa gattttaggt cattaaatga    3840
ttcaacaaat agaacaaaga aacacacagc tcatttctca aaaaaagggg aggaagaaaa    3900
cttggaaggc ttgggaaatc aaaccaagca aattgtagag aaatatgcat gcaccacaag    3960
gatatctcct aatacaagcc agcagaattt tgtcacgcaa cgtagtaaga gagctttgaa    4020
acaattcaga ctcccactag aagaaacaga acttgaaaaa aggataattg tggatgacac    4080
ctcaacccag tggtccaaaa acatgaaaca tttgaccccg agcaccctca cacagataga    4140
ctacaatgag aaggagaaag gggccattac tcagtctccc ttatcagatt gccttacgag    4200
gagtcatagc atccctcaag caaatagatc tccattaccc attgcaaagg tatcatcatt    4260
tccatctatt agacctatat atctgaccag ggtcctattc caagacaact cttctcatct    4320
tccagcagca tcttatagaa agaaagattc tggggtccaa gaaagcagtc atttcttaca    4380
aggagccaaa aaaaataacc tttctttagc cattctaacc ttggagatga ctggtgatca    4440
aagagaggtt ggctccctgg ggacaagtgc acaaattca gtcacataca agaaagttga      4500
gaacactgtt ctcccgaaac cagacttgcc caaaacatct ggcaaagttg aattgcttcc    4560
aaaagttcac atttatcaga aggacctatt ccctacggaa actagcaatg ggtctcctgg    4620
ccatctggat ctcgtggaag ggagccttct tcagggaaca gagggagcga ttaagtggaa    4680
tgaagcaaac agacctggaa aagttccctt tctgagagta gcaacagaaa gctctgcaaa    4740
gactccctcc aagctattgg atcctcttgc ttgggataac cactatggta ctcagatacc    4800
aaaagaagag tggaaatccc aagagaagtc accagaaaaa acagcttta agaaaaagga      4860 taccattttg tccctgaacg cttgtgaaag caatcatgca atagcagcaa taatgagggg    4920
acaaaataag cccgaaatag aagtcacctg ggcaaagcaa ggtaggactg aaaggctgtg    4980
ctctcaaaac ccaccagtct tgaaacgcca tcaacgggaa ataactcgta ctactcttca    5040
gtcagatcaa gaggaaattg actatgatga taccatatca gttgaaatga agaaggaaga    5100
ttttgacatt tatgatgagg atgaaaatca gagcccccgc agctttcaaa agaaaacacg    5160
```

```
acactatttt attgctgcag tggagaggct ctgggattat gggatgagta gctccccaca    5220
tgttctaaga aacagggctc agagtggcag tgtccctcag ttcaagaaag ttgttttcca    5280
ggaatttact gatggctcct ttactcagcc cttataccgt ggagaactaa atgaacattt    5340
gggactcctg gggccatata taagagcaga agttgaagat aatatcatgg taactttcag    5400
aaatcaggcc tctcgtccct attccttcta ttctagcctt atttcttatg aggaagatca    5460
gaggcaagga gcagaaccta gaaaaaactt tgtcaagcct aatgaaacca aaacttactt    5520
ttggaaagtg caacatcata tggcacccac taaagatgag tttgactgca aagcctgggc    5580
ttatttctct gatgttgacc tggaaaaaga tgtgcactca ggcctgattg gaccccttct    5640
ggtctgccac actaacacac tgaaccctgc tcatgggaga caagtgacag tacaggaatt    5700
tgctctgttt ttcaccatct ttgatgagac caaaagctgg tacttcactg aaaatatgga    5760
aagaaactgc agggctccct gcaatatcca gatggaagat cccactttta aagagaatta    5820
tcgcttccat gcaatcaatg gctacataat ggatacacta cctggcttag taatggctca    5880
ggatcaaagg attcgatggt atctgctcag catgggcagc aatgaaaaca tccattctat    5940
tcatttcagt ggacatgtgt tcactgtacg aaaaaaagag gagtataaaa tggcactgta    6000
caatctctat ccaggtgttt ttgagacagt ggaaatgtta ccatccaaag ctggaatttg    6060
gcgggtggaa tgccttattg gcgagcatct acatgctggg atgagcacac tttttctggt    6120
gtacagcaat aagtgtcaga ctcccctggg aatggcttct ggacacatta gagattttca    6180
gattacagct tcaggacaat atggacagtg ggccccaaag ctggccagac ttcattattc    6240
cggatcaatc aatgcctgga gcaccaagga gcccttttct tggatcaagg tggatctgtt    6300
ggcaccaatg attattcacg gcatcaagac ccagggtgcc cgtcagaagt tctccagcct    6360
ctacatctct cagtttatca tcatgtatag tcttgatggg aagaagtggc agacttatcg    6420
aggaaattcc actggaacct taatggtctt ctttggcaat gtggattcat ctgggataaa    6480
acacaatatt tttaaccctc caattattgc tcgatacatc cgtttgcacc caactcatta    6540
tagcattcgc agcactcttc gcatggagtt gatgggctgt gatttaaata gttgcagcat    6600
gccattggga atggagagta aagcaatatc agatgcacag attactgctt catcctactt    6660
taccaatatg tttgccacct ggtctccttc aaaagctcga cttcacctcc aagggaggag    6720
taatgcctgg agacctcagg tgaataatcc aaaagagtgg ctgcaagtgg acttccagaa    6780
gacaatgaaa gtcacaggag taactactca gggagtaaaa tctctgctta ccagcatgta    6840
tgtgaaggag ttcctcatct ccagcagtca agatggccat cagtggactc tcttttttca    6900
gaatggcaaa gtaaaggttt ttcagggaaa tcaagactcc ttcacacctg tggtgaactc    6960
tctagaccca ccgttactga ctcgctacct tcgaattcac ccccagagtt gggtgcacca    7020
gattgccctg aggatggagg ttctgggctg cgaggcacag gacctctact gagtcgacct    7080
cc                                                                    7082
```